US011944628B2

(12) United States Patent
Kishnani et al.

(10) Patent No.: US 11,944,628 B2
(45) Date of Patent: Apr. 2, 2024

(54) METHODS FOR THE USE OF LOW-DOSE IMMUNE MODULATORS TRANSIENTLY FOR TREATING PATIENTS UNDERGOING PROTEIN REPLACEMENT THERAPY

(71) Applicant: Duke University, Durham, NC (US)

(72) Inventors: Priya S. Kishnani, Durham, NC (US); Zoheb B. Kazi, Durham, NC (US); Ankit K. Desai, Durham, NC (US)

(73) Assignee: Duke University, Durham, NC (US)

( * ) Notice: Subject to any disclaimer, the term of this patent is extended or adjusted under 35 U.S.C. 154(b) by 85 days.

(21) Appl. No.: 16/612,976

(22) PCT Filed: May 11, 2018

(86) PCT No.: PCT/US2018/032422
§ 371 (c)(1),
(2) Date: Nov. 12, 2019

(87) PCT Pub. No.: WO2018/209300
PCT Pub. Date: Nov. 15, 2018

(65) Prior Publication Data
US 2020/0078361 A1  Mar. 12, 2020

Related U.S. Application Data

(60) Provisional application No. 62/505,244, filed on May 12, 2017.

(51) Int. Cl.
A61P 37/02    (2006.01)
A61K 31/519   (2006.01)
A61K 38/47    (2006.01)

(52) U.S. Cl.
CPC ............ A61K 31/519 (2013.01); A61K 38/47 (2013.01); A61P 37/02 (2018.01)

(58) Field of Classification Search
None
See application file for complete search history.

(56) References Cited

U.S. PATENT DOCUMENTS

| 8,809,282 | B2 * | 8/2014 | Kishnani | A61P 3/00 |
| | | | | 514/21.91 |
| 9,592,247 | B2 | 3/2017 | Kishnani et al. | |
| 2014/0135337 | A1 * | 5/2014 | Joseph | A61P 25/00 |
| | | | | 514/249 |
| 2015/0037329 | A1 * | 2/2015 | Kishnani | A61K 38/1722 |
| | | | | 424/133.1 |
| 2015/0086530 | A1 | 3/2015 | Greene et al. | |
| 2020/0405722 | A1 | 12/2020 | Kishnani et al. | |

FOREIGN PATENT DOCUMENTS

WO  2016161086 A1  10/2016
WO  2017117407      7/2017

OTHER PUBLICATIONS

Mendelsohn, N.J. et al. 2009. Elimination of antibodies to recombinant enzyme in Pompe's disease. New England Journal of Medicine 360(2): 194-195. specif. pp. 194, 195.*
Banugaria, S.G. et al. 2013. Algorithm for the early diagnosis and treatment of patients with cross reactive immunologic material-negative classic infantile Pompe disease: a step towards improving the efficacy of ERT. PLoS One 8(6): 1-11; specif. pp. 1, 2, 4, 10.*
Begg, E.J. et al. 2011. A unified pharmacokinetic approach to individualized drug dosing. British Journal of Clinical Pharmacology 73(3): 335-339; specif. p. 335.*
Desai, A.K. et al. 2019. Immunological challenges and approaches to immunomodulation in Pompe disease: a literature review. Annals of Translational Medicine 7(13): 1-21; specif. pp. 4, 5.*
Joly, M.S. et al. 2014. Transient low-dose methotrexate generates B regulatory cells that mediate antigen-specific tolerance to alglucosidase alfa. The Journal of Immunology 193: 3947-3958; specif. pg. 3947.*
Raben, N. et al. 2003. Enzyme replacement therapy in the mouse model of Pompe disease. Molecular Genetics and Metabolism 80: 159-169; specif. pg. 159 (Year: 2003).*
Bali et al., "Predicting cross-reactive immunological material (CRIM) status in Pompe disease using GAA mutations: lessons learned from 10 years of clinical laboratory testing experience," Am. J Med Genet. C. Semin. Med. Genet. 160C:40-49 (2012).
Banugaria et al., "The impact of antibodies on clinical outcomes in diseases treated with therapeutic protein: lessons learned from infantile Pompe disease," Genet. Med. 13:729-736 (2011).
Banugaria et al., "Algorithm for the early diagnosis and treatment of patients with cross reactive immunologic material-negative classic infantile pompe disease: a step towards improving the efficacy of ERT," PLos One 8:e67052 (2013).
Berrier et al., "CRIM-negative infantile Pompe disease: characterization of immune responses in patients treated with ERT monotherapy," Genet. Med. 17:912-18 (2015).
Cousens et al., "Teaching tolerance: New approaches to enzyme replacement therapy for Pompe disease," Hum. Vaccin. Immunother. 8: 1459-1464 (2012).
Elder at al., "B-Cell depletion and immunomodulation before initiation of enzyme replacement therapy blocks the immune response to acid alpha-glucosidase in infantile-onset Pompe disease," J Pediatr. 163:847-854 e841 (2013).
Garman et al., "Methotrexate reduces antibody responses to recombinant human alpha-galactosidase A therapy in a mouse model of Fabry disease," Clin. Exp. Imunol. 137:496-502 (2004).
Genzyme Corp. Lumizyme® (alglucosidase alfa) Prescribing Information. Aug. 2014.
Joly et al., "Transient low-dose methotrexate generates B regulatory cells that mediate antigen-specific tolerance to alglucosidase alfa," J Immunol. 193:3947-3958 (2014).
Joseph et al., "Immune tolerance induction to enzyme-replacement therapy by co-administration of short-term, low-dose methotrexate in a murine Pompe disease model," Clin. Exp. Immunol. 152: 138-146 (2008).

(Continued)

Primary Examiner — Adam Weidner
Assistant Examiner — Sharon M. Papciak
(74) Attorney, Agent, or Firm — POLSINELLI PC

(57) ABSTRACT

The present disclosure provides compositions and methods for inducing immune tolerance in subjects suffering from metabolic diseases.

17 Claims, 12 Drawing Sheets

(56) References Cited

OTHER PUBLICATIONS

Kazi et al., "Sustained immune tolerance induction in enzyme replacement therapy-treated CRIM-negative patients with infantile Pompe disease," JCI Insight 2(16):e94328 (2017).
Kishnani et al., "Chinese hamster ovary cell-derived recombinant human acid alpha-glucosidase in infantile-onset Pompe disease," J Pediatr. 149:89-97 (2006).
Kishnani et al., "Cross-reactive immunologic material status affects treatment outcomes in Pompe disease infants," Mol Genet Metab 99:26-33 (2010).
Lim et al., "Immunomodulation to enzyme replacement therapy with tolerogenic nanoparticles containing rapamycin in a murine model of Pompe disease," Mol. Genet. Metab. 120:S83-S84 (2017).
Mauri et al., "The expanding family of regulatory B cells," Int. Immunol. 27:479-86 (2015).
Messinger et al., "Successful immune tolerance induction to enzyme replacement therapy in CRIM-negative infantile Pompe disease," Genet. Med. 14:135-142 (2012).
Stenger et al., "Immune Tolerance Strategies in Siblings with Infantile Pompe Disease-Advantages for a Preemptive Approach to High-Sustained Antibody Titers," Mol. Genet. Metab. Rep. 4:30-34 (2015).
Sun et al., "Non-depleting anti-CD4 monoclonal antibody induces immune tolerance to ERT in a murine model of Pompe disease," Mol. Genet. Metab. Rep. 1:446-450 (2014).
Written Opinion dated Aug. 10, 2018 for PCT/US2018/032422 filed May 11, 2018 (Inventors—Kishnani et al. // Applicant—Duke University) (6 pages).
International Search Report dated Aug. 10, 2018 for PCT/US2018/032422 filed May 11, 2018 (Inventors—Kishnani et al. // Applicant—Duke University) (2 pages).
Product Monograph for Myozyme (alglucosidase alfa—recombinant human acid alpha glucosidase)—Revision dated Dec. 16, 2016—54 pages—published by Sanofi Genzyme—available at https://products.sanofi.ca/en/myozyme-en.pdf.

* cited by examiner

METHODS FOR THE USE OF LOW-DOSE IMMUNE MODULATORS TRANSIENTLY FOR TREATING PATIENTS UNDERGOING PROTEIN REPLACEMENT THERAPY

CROSS-REFERENCE TO RELATED APPLICATIONS

This application is a U.S. National Phase of International Application No. PCT/US2018/032422, filed on May 11, 2018, which claims priority to U.S. Provisional Patent Application No. 62/505,244, filed on May 12, 2017, the disclosure of each of which is hereby incorporated by reference in their entireties.

BACKGROUND

Pompe disease, also known as glycogen storage disease type II (OMIM 232300) or acid maltase deficiency, is an autosomal recessive lysosomal storage disorder in which deficiency of the lysosomal enzyme acid α-glucosidase (GAA, EC 3.2.1.20), results in a build-up of glycogen in cardiac, skeletal, and smooth muscle of affected individuals. Classic infantile-onset Pompe disease (IOPD) presents in the first few days to weeks of life, with symptoms of hypotonia, cardiomyopathy, and respiratory insufficiency. Without treatment, death usually occurs before the age of 2 years. Pompe disease phenotypes without infantile cardiomyopathy are generally classed either atypical IOPD with onset before 12 months of age without cardiomyopathy or late-onset Pompe disease (LOPD) with onset in childhood (>1 to 12 years), adolescence, or adulthood.

Alglucosidase alfa (recombinant human GAA; rhGAA) was approved for enzyme replacement therapy (ERT) in Pompe disease in 2006; its administration has been shown to improve overall and ventilator-free survival in IOPD, with improved overall clinical outcomes and many long-term survivors reaching adolescence. However, response to ERT is often affected by an immune response, which may increase infusion-associated reactions (IgE mediated, or complement mediated), lead to mistargeting of delivered enzyme by facilitating enzyme uptake in non-target cells (IgG mediated), block ERT's target cell entry, block catalytic activity of ERT, and/or reduce clinical efficacy (IgG mediated). Treatment response has been shown to be related to the patient's endogenous enzyme, commonly referred to as cross-reactive immunologic material (CRIM) status, with CRIM-negative patients developing high and sustained anti-rhGAA immunoglobulin G (IgG) antibody titers (HSAT; defined as titers of ≥51,200 at ≥2 time points at or beyond six months on rhGAA) and having a poor outcome in response to ERT compared with CRIM-positive patients. HSAT develops in a majority of cross-reactive immunological material (CRIM)-negative, ~40% of CRIM-positive patients with IOPD and 10% of patients with LOPD, leading to a poor response to treatment and a subsequent clinical decline.

Treatment response has been shown to be related to the degree of abnormality of the patient's endogenous enzyme, commonly referred to as CRIM status, with CRIM-negative patients having a poor outcome in response to ERT compared with CRIM-positive patients. CRIM-negative patients cannot form the native enzyme and usually possess two severe GAA pathogenic variants; their immune systems recognize ERT as foreign and, as a result, form anti-rhGAA IgG antibodies. In contrast, CRIM-positive patients have some residual native enzyme, whether functional or non-functional, and are more likely to develop lower or no levels of anti-rhGAA IgG.

CRIM-negative patients account for ~25-32% of all patients with IOPD, and are likely to have a poor clinical outcome when treated with ERT alone. In contrast, CRIM-positive patients have some residual native enzyme, whether functional or non-functional, and are more likely to develop lower anti-rhGAA IgG titers or none.

In a retrospective analysis by Banugaria et al. (2011) *Genet. Med.* 13:729-736, 39% (9 of 23) CRIM-positive patients with IOPD had high antibody titers and their clinical outcomes were poor, similar to those in CRIM-negative patients; thus it was established that antibody status affects ERT response. At present, there are no predictive factors to determine which CRIM-positive patients will develop HSAT or sustained intermediate titers (SIT; defined as titers of ≥12,800 and <51,200 within the first year on rhGAA).

Immune tolerance induction (ITI) protocols have been established as an approach to minimize the development of anti-drug antibodies and maintain low or absent antibody titers over time. Protocols for ITI using various immuno-modulating drugs have been studied to prevent development of an immune response in ERT-naïve patients and for therapy to decrease existing anti-rhGAA antibodies in ERT-treated patients with already established immune responses. However, studies in the largest number of CRIM-negative patients naïve to ERT therapy have prophylactically combined rituximab and methotrexate (e.g. one course of rituximab 375 mg/m$^2$ IV weekly four times; methotrexate 0.4 mg/kg SC or PO daily for 3 days along with first three ERT infusions, thus a total of 9 doses), with or without intravenous immunoglobulin, in efforts to preempt an immune response. In the past, there was no success in patients with an entrenched immune response and antibody titers persisted after multiple immune modulating treatment regimens. Addition of the plasma cell-targeting agent bortezomib or other therapies in patients with established HSAT has proven successful in minimizing antibody titers, yet required prolonged immunosuppression arising from the use of maintenance doses of rituximab and methotrexate along with bortezomib.

A short course of prophylactic ITI in CRIM-negative IOPD patients has improved clinical outcomes as compared with ERT monotherapy by preempting the development of HSAT and thus preventing the consequent loss of ERT efficacy. A prior study by Banugaria et al., started a three-drug ITI regimen (methotrexate, rituximab, and intravenous immunoglobulin) concurrently with ERT in 7 CRIM-negative classic IOPD patients. (Banugaria et al. (2013) *PLos One* 8:e67052). Four patients never seroconverted (developed antibodies), 1 patient died of respiratory failure, and 2 patients required additional ITI courses, which left their antibody titers lower than in ERT-treated CRIM-negative infants without ITI. A follow-up study with the same three-drug ITI regimen in 19 CRIM-negative patients, including the 7 patients in the 2013 Banugaria et al. study, showed that 15 of 19 patients either did not seroconvert or maintained low antibody titers, in contrast to the natural course of CRIM-negative patients on ERT monotherapy. Only one of these 19 patients broke tolerance and developed HSAT. (Kazi et al. (2017) *JCI Insight* 2). This patient was subsequently rescued using a bortezomib-based ITI protocol. The same prophylactic ITI regimen successfully induced tolerance in the CRIM-positive younger sibling of a CRIM-positive Pompe patient who had developed HSAT on ERT monotherapy. (Stenger et al. (2015) *Mol. Genet. Metab. Rep.*

4:30-34). Prophylactic ITI protocols concurrent with ERT initiation are used increasingly by treating physicians worldwide and are considered a standard of care for CRIM-negative patients.

A subset of CRIM-positive patients also develop a sustained immune response, (Banugaria et al. (2015) *Genet. Med.* 13:729-736) and it is difficult to predict which individuals will develop antibodies (seroconvert) or go on to develop HSAT or SIT. Anti-rhGAA antibody titers ≥12,800, were associated with an increase in ERT clearance in a pharmacokinetic study reported in the alglucosidase alfa prescribing information. (Genzyme Corp. LUMIZYME® (alglucosidase alfa) Prescribing Information. August 2014). Clinical response to ERT may be better conserved by preempting HSAT/SIT than by striving to reduce it once it occurs. (Stenger et al. (2015) *Mol. Genet. Metab. Rep.* 4:30-34). Once antibodies develop, it remains a challenge in the field of therapeutic proteins to control these responses, thus every effort to prevent the development of these deleterious antibodies is important. Thus, study of prophylactic ITI regimens at ERT initiation merits extension into CRIM-positive patients, given that a large subset of them develop significant antibodies likely to have deleterious clinical impact.

Preclinically, a transient low dose of methotrexate alone co-initiated with ERT sustainably reduced anti-rhGAA IgG response in a GAA knock-out mouse model of Pompe disease. (Joseph et al. (2008) *Clin. Exp. Immunol.* 152:138-146). Studies in wild-type and GAA knock-out mice suggest a mechanism for methotrexate ITI that involves an IL-10 and B regulatory cell-dependent environment. (Joly et al. (2014) *J. Immunol.* 193:3947-3958; Mauri et al. (2015) *Int. Immunol.* 27:479-86). Other immune tolerance-inducing mechanisms may also come into play.

In the light of these results and given that methotrexate has a favorable safety profile in the doses proposed, is inexpensive and widely accessible, and can be administered only during the initial phases of therapy, the first human protocol was initiated incorporating transient use of methotrexate at the initiation phase of ERT in naïve patients with IOPD or LOPD. Described herein are novel methods to induce immune tolerance using a transient, low dose immune modulation regimen patients undergoing ERT.

BRIEF SUMMARY OF THE INVENTION

The present disclosure relates to methods and compositions of improving the efficacy of enzyme replacement therapy "ERT" in a subject.

One aspect of the present disclosure provides a method of inducing immune tolerance to a therapeutic agent in a subject suffering from a metabolic disorder, said method comprising administering to the subject a therapeutically effective amount of an immune modulator and the therapeutic agent such that immune tolerance is induced in the subject.

In some embodiments of the present disclosure, therapeutic agent is a proteinaceous replacement for a protein that is deficient or absent in the subject. In some embodiments of the present disclosure, the therapeutic agent is a proteinaceous replacement for acid alpha-glucosidase (GAA). In other embodiments of the present disclosure, the proteinaceous replacement for acid alpha-glucosidase (GAA) is recombinant human GAA (rhGAA).

In some embodiments of the present disclosure, the metabolic disorder is Fabry Disease, Gaucher disease, GSDs types I-VII, IX, XI, XII and XIII, cardiac glycogenesis due to AMP-activated protein kinase gamma subunit 2 deficiency, MPS diseases including MPS I (Hurler, Hurler-Scheie, or Scheie syndrome), MPS II (Hunter disease), and MPS VI (Maroteaux-Lamy syndrome), Pompe Disease, or Wolman disease. In other embodiments of the present disclosure, the metabolic disease comprises Pompe Disease.

In some embodiments of the present disclosure, the subject is a treatment-naïve cross-reactive immunological material (CRIM)-positive or a treatment-naïve CRIM-negative lysosomal storage disease patient.

In some embodiments of the present disclosure, the immune modulator is methotrexate, rituximab, intravenous gamma globulin, or bortezomib.

In some embodiments of the present disclosure, the immune modulator is administered at a transient low-dose. In other embodiments of the present disclosure, the immune modulator is administered at a dose of about 0.1 mg/kg body weight to about 0.6 mg/kg body weight. In yet other embodiments of the present disclosure, the immune modulator is administered at a dose of about 0.4 mg/kg body weight.

In some embodiments of the present disclosure, the immune modulator is administered concurrently with the therapeutic agent.

In some embodiments of the present disclosure, the immune modulator is administered at about a daily dose of 0.4 mg/kg body weight for 3 to 5 cycles, with three days per cycle. In other embodiments of the present disclosure, the immune modulator is administered at about a daily dose of 0.4 mg/kg body weight for a minimum of 3 cycles, with three days per cycle.

In some embodiments of the present disclosure, the immune modulator is administered orally about one hour before the therapeutic agent. In other embodiments, the immune modulator is administered subcutaneously about 15 minutes before the therapeutic agent.

Another aspect of the present disclosure provides, a method of reducing or preventing the formation of titers of antibodies for a therapeutic agent in a subject suffering from a metabolic disorder, said method comprising administering to the subject a therapeutically effective amount of an immune modulator and the therapeutic agent such that the antibody formation is reduced or prevented.

In some embodiments of the present disclosure, the therapeutic agent is a proteinaceous replacement for acid alpha-glucosidase (GAA). In other embodiments of the present disclosure, the proteinaceous replacement for acid alpha-glucosidase (GAA) is recombinant human GAA (rhGAA).

In some embodiments of the present disclosure, the metabolic disorder is Fabry Disease, Gaucher disease, GSDs types I-VII, IX, XI, XII and XIII, cardiac glycogenesis due to AMP-activated protein kinase gamma subunit 2 deficiency, MPS diseases including MPS I (Hurler, Hurler-Scheie, or Scheie syndrome), MPS II (Hunter disease), and MPS VI (Maroteaux-Lamy syndrome), Pompe Disease, or Wolman disease.

In some embodiments of the present disclosure, the immune modulator is methotrexate, rituximab, intravenous gamma globulin, or bortezomib. In other embodiments of the present disclosure, the immune modulator is administered at a transient low-dose.

In some embodiments of the present disclosure, the method of reducing or preventing the formation of titers of antibodies for a therapeutic agent in a subject suffering from a metabolic disorder, said method comprising administering to the subject a therapeutically effective amount of an immune modulator and the therapeutic agent prevents the formation of high and sustained anti-rhGAA immunoglobulin G (IgG) antibody titers or the formation of sustained intermediate titers.

BRIEF DESCRIPTION OF THE DRAWINGS

The foregoing aspects and other features of the invention are explained in the following description, taken in connection with the accompanying drawings, wherein:

FIG. 3A is a graph showing each patient's trajectory graphed individually as a curve, with the titer subgroups indicated by shape: HSAT (triangle); IT (upside down triangle); and LT (circle). The comparators' immune responses by titer group are graphed separately in FIG. 3B-3D for legibility. FIG. 3B is a graph showing the comparators' immune responses for the HSAT group (n=5). FIG. 3C is a graph showing the comparators' immune responses for the SIT group (n=7). FIG. 3D is a graph showing the comparators' immune response for the LT group (n=25). Positive titers <100 are shown as titers of 50.

FIG. 4A is a graph showing the anti-rhGAA antibody titers for the IOPD patients. FIG. 4B is a graph showing the anti-rhGAA antibody titers for the atypical IOPD patients (AIOP). FIG. 4C is a graph showing the anti-rhGAA antibody titers for the late-onset Pompe disease patients (LOPD). *Indicates positive titers <100.

DETAILED DESCRIPTION OF THE INVENTION

Figure 1:
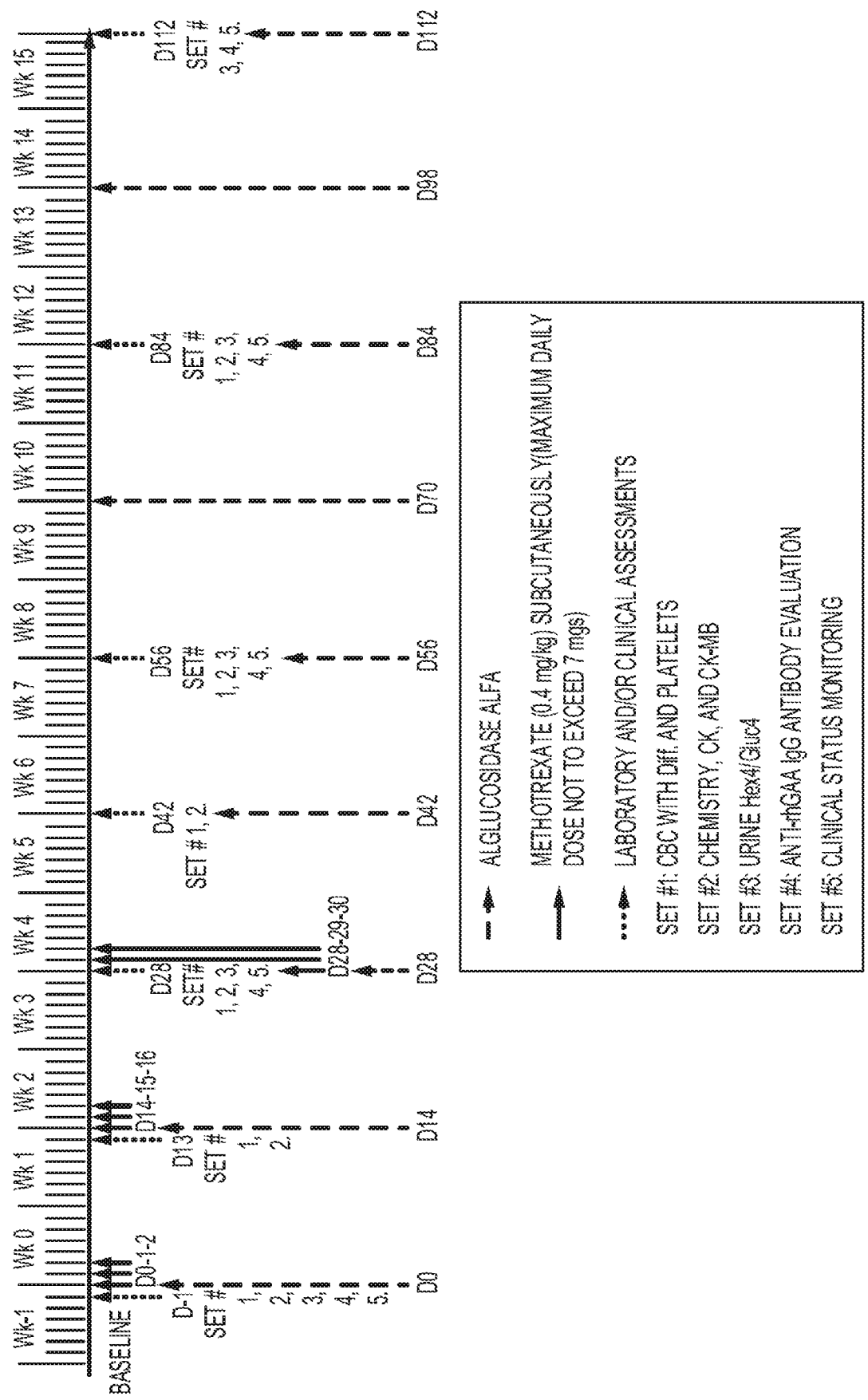
FIG. 1 is a schematic showing the study timeline for infantile Pompe disease patients receiving ERT infusions every other week.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

As used herein, the term "and/or" includes any and all combinations of one or more of the associated listed items.

As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "about" in association with a numerical value means that the numerical value can vary plus or minus by 5% or less of the numerical value.

Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of aspects and embodiments are disclosed. Each of these has individual benefit and each can also be used in conjunction with one or more, or in some cases all, of the other disclosed aspects and embodiments, whether specifically delineated or not. Accordingly, for the sake of clarity, this description will refrain from repeating every possible combination of the individual aspects and embodiments in an unnecessary fashion. Nevertheless, the specification and claims should be read with the understanding that such combinations are implicitly disclosed, and are entirely within the scope of the invention and the claims, unless otherwise specified.

One aspect of the present disclosure provides a method of inducing immune tolerance to a therapeutic agent in a subject suffering from a metabolic disorder, said method comprising, consisting of, or consisting essentially administering to the subject a therapeutically effective amount of an immune modulator and the therapeutic agent such that immune tolerance is induced in the subject.

As used herein, the term "metabolic disorder" refers to any disorder occurs from an inherited single gene anomaly or when abnormal chemical reactions in the body alter the normal metabolic process. Examples of metabolic disorders include, but are not limited to, lysosomal storage disease, glycogen storage disease, gluconeogenesis disorder, galactose metabolism disorder (e.g., galactosemia), aminoacidopathies (e.g., phenylketonuria, maple syrup urine disease, tyrosinemia type 1), organic acidemias (e.g., methylmalonic academia), fatty acid metabolism disorder (e.g., MCAD), urea cycle disorder (e.g., OTC, citrullinemia, lipoprotein metabolism disorder (e.g., familial hypercholesterolemia), bilirubin metabolism disorder (e.g., Crigler-Najjar), purine and pyrimidine metabolism disorder (e.g., severe combined immunodeficiency Gout, Lesch-Nyan syndrome), vitamin metabolism disorder (e.g., biotinidase deficiency), peroxisomal disorder (e.g., Zellweger syndrome), and heme biosynthesis disorder (e.g., acute intermittent *porphyria*).

The term "lysosomal storage disease" or "LSD" refers to the group of rare inherited metabolic disorders that result from defects in lysosomal functions. Examples include, but are not limited to, Fabry Disease, Gaucher disease, MPS diseases including MPSI I (Hurler, Hurler-Scheie, or Scheie syndrome), MPS II (Hunter disease), and MPS VI (Maroteaux-Lamy syndrome), Pompe Disease (GSD II), Wolman disease, Niemann Pick and the like.

In certain embodiments, the lysosomal storage disease comprises Pompe Disease. Pompe disease includes patients having classic IOPD, atypical IOPD, or LOPD. Classic IOPD typically has an age at onset ≤12 months of age with cardiomyopathy, atypical IOPD typically has an age at onset ≤12 months of age without cardiomyopathy or >12 months to <12 years of age, and LOPD typically has symptom onset at >12 years of age.

The term "glycogen storage disease" or "GSD" refers to any number of metabolic disorders caused by enzyme deficiencies affecting glycogen synthesis, glycogen breakdown or glycolysis (glucose breakdown), typically within the muscles, liver cells, or other cells. Examples of glycogen storage diseases include, but are not limited to, GSDs types I-VII, IX, XI, XII and XIII, and cardiac glycogenesis due to AMP-activated protein kinase gamma subunit 2 deficiency.

As used herein, the term "therapeutic agent" refers to any compound (e.g., protein, enzyme, peptide, nucleic acid, chemical compound, small molecule, pharmaceutical formulation, or combinations thereof) that is capable of producing a beneficial effect in the subject. Some therapeutic agents are biological in origin, and can include components of plants and minerals as well as animal products. Other therapeutic agents are synthetic and produced in a laboratory environment (e.g., recombinantly expressed proteins).

In some embodiments, the therapeutic agent is a proteinaceous replacement. The term "proteinaceous" as used herein refers to a molecule relating to, containing, resembling, or being a protein. A protein is a large biomolecule comprising one or more chains of amino acid residues. A protein can be catalytically inactive or active (e.g., an enzyme).

As used herein, the term "proteinaceous replacement" refers to a protein that can be administered to a subject to increase the bioavailability of a protein that is deficient or absent in a subject. Proteinaceous replacement therapeutic agents can be used in therapies that include, but art not limited to, protein replacement therapy, enzyme replacement therapy, gene therapy, and for treatments using biologics.

As used herein, the terms "protein replacement therapy" and "enzyme replacement therapy (ERT)" refers to a medical treatment which increases the bioavailability of an enzyme that is deficient or absent in the body of the subject. The term "protein replacement therapy" as used herein also includes gene therapy and therapy with biologic drugs.

Lysosomal storage diseases are a primary application of ERT. There are around 50 lysosomal storage diseases with even more still being discovered. Lysosomal storage disorders arise because of genetic mutations that prevent the production of certain enzymes used in the lysosomes, which break down different macromolecules and proteins. The missing enzyme often leads to a build-up of the substrate within the body, resulting in a variety of symptoms, many of which are severe and can affect the skeleton, brain, skin, eyes, heart, lungs, liver, skin and the central nervous system. Increasing the concentration of the missing enzyme within the subject has been shown to improve the subject's normal cellular metabolic processes and reduce substrate concentration in the subject. Currently, ERT is available for lysosomal storage diseases such as Gaucher disease, Fabry disease, MPS I, MPS II (Hunter syndrome), MPS VI, Niemann Pick type B, Batten disease, Pompe disease, and Wolman disease. ERT does not remedy the underlying genetic defect, but it increases the concentration of the enzyme that the subject is lacking.

The particular proteinaceous replacement therapeutic agent will depend on the specific disorder to be treated. Examples of proteinaceous therapeutic agents include, but are not limited to a proteinaceous replacement for acid alpha-glucosidase (GAA), α-Sialidase, Galactosialidosis, α-Mannosidase, β-Mannosidase, Glycosylasparaginase, α-Fucosidase, α-N-Acetylglucosaminidase, β-Galactosidase, β-Hexosaminidase α-subunit, β-Hexosaminidase β-subunit, GM2 activator protein, Glucocerebrosidase, Saposin C, Arylsulfatase A, Saposin B, Formyl-Glycin generating enzyme, β-Galactosylceramidase (Krabbe), α-Galactosidase A, Iduronate sulfatase, α-Iduronidase, Heparan N-sulfatase, Acetyl-CoA transferase, N-acetyl glucosaminidase, β-glucuronidase, N-acetyl glucosamine 6-sulfatase, N-Acetylgalactosamine 4-sulfatase, Galactose 6-sulfatase, Hyaluronidase, Acid sphingomyelinase, Acid ceramidase, Acid lipase, Cathepsin K, Tripeptidyl peptidase, Palmitoyl-protein thioesterase, Cystinosin, Sialin, Phosphotransferase γ-subunit, Mucolipin-1(cation channel), LAMP-2, NPC1, CLN3, CLN 6, CLN 8, LYST, MYOV, RAB27A, Melanophili, and AP3 β-subunit. In some embodiments, the proteinaceous replacement for acid alpha-glucosidase (GAA) is recombinant human GAA (rhGAA).

The therapeutic agent described herein can be administered by any suitable route of administration. In certain embodiments, the therapeutic agent is administered intravenously, subcutaneously, transdermally, intradermally, intramuscularly, orally, transcutaneously, intraperitoneally (IP), or intravaginally.

The therapeutic agent of the invention can be administered to the subject either naked or in conjunction with a delivery reagent. Examples of delivery reagents for administration in conjunction with the therapeutic agent s include, but are not limited to, Mirus Transit TKO lipophilic reagent, lipofectin, lipofectamine, cellfectin, polycations (e.g., polylysine), micelles, PEGylated liposome or nanoparticles, oligonucleotide nanoparticles, cyclodextrin polymer (CDP)-based nanoparticles, biodegradable polymeric nanoparticles formulated with poly-(D,L-lactide-co-glycolide) (PLGA), Poly-lactic acid (PLA), or N-(2-hydroxypropyl)methacrylamide (HPMA), lipid nanoparticles (LNP), stable nucleic acid lipid particles (SNALP), vitamin A coupled lipid nanoparticles, and combinations thereof.

One skilled in the art can also readily determine an appropriate dosage regimen for administering the therapeutic agent to a given subject.

In another embodiment, the therapeutic agent is formulated as a pharmaceutical composition prior to administering to a subject, according to techniques known in the art. Pharmaceutical compositions of the present invention are characterized as being at least sterile and pyrogen-free. As used herein, "pharmaceutical formulations" or "pharmaceutical compositions" include formulations for human and veterinary use.

As used herein the terms "immune tolerance," "immunological tolerance," and "immunotolerance" refers to a state of unresponsiveness of the immune system to substances (e.g., a therapeutic agent) that have the capacity to elicit an immune response in a subject. Immune tolerance is induced by prior exposure to a specific antigen. Immune tolerance can be determined in a subject by measuring antibodies against a particular antigen. Low or absent antibody titers over time is an indicator of immune tolerance. For example, in some embodiments, immune tolerance can be established by having IgG antibody titers of less than or equal to about 12,000, 11,500, 11,000, 10,500, 10,000, 9,500, 9,000, 8,500, 8,000, 7,500, 7,000, 6,500, or 6,000 within the first year of ERT. In some embodiments, an example of a low titer is an rhGAA IgG antibody titer less than 12,800 within the first year of ERT.

As used herein, the term "immune modulator" refers to an agent that is capable of adjusting a given immune response to a desired level, as in immunopotentiation, immunosuppression, or induction of immunologic tolerance. Examples of immune modulators include but are not limited to, betamethasone dipropionate, betamethasone valerate, fluocinolone acetonide, triamcinolone acetonide, prednisone, methylprednisolone, prednisolone indomethacin, sulindac, ibuprofen, aspirin, naproxen, tolmetin, azathioprine, cyclosporine, cyclophosphamide, deoxyspergualin, bredinin, didemnin B, methotrexate, rituximab (anti-CD20 monoclonal antibody), intravenous gamma globulin (IVIG), bortezomib, thalidomide, and sirolimus.

The immune modulator described herein can be administered by any suitable route of administration. In certain embodiments, the immune modulator is administered intravenously, subcutaneously, transdermally, intradermally, intramuscularly, orally, transcutaneously, intraperitoneally (IP), or intravaginally.

The immune modulator of the invention can be administered to the subject either naked or in conjunction with a delivery reagent. Examples of delivery reagents for administration in conjunction with the immune modulator include, but are not limited to, Mirus Transit TKO lipophilic reagent, lipofectin, lipofectamine, cellfectin, polycations (e.g., polylysine), micelles, PEGylated liposome or nanoparticles, oligonucleotide nanoparticles, cyclodextrin polymer (CDP)-based nanoparticles, biodegradable polymeric nanoparticles formulated with poly-(D,L-lactide-co-glycolide) (PLGA), Poly-lactic acid (PLA), or N-(2-hydroxypropyl)methacrylamide (HPMA), lipid nanoparticles (LNP), stable nucleic acid lipid particles (SNALP), vitamin A coupled lipid nanoparticles, rapamycin-carrying synthetic vaccine particles (SVP rapa), and combinations thereof.

One skilled in the art can also readily determine an appropriate dosage regimen for administering the immune modulator to a given subject.

In all treatment situations described herein (e.g., protein replacement, gene therapy, therapy with biologics, etc.) the immune modulators described herein or elsewhere can be used in connection with additional immunomodulating therapeutic agents, or their derivatives, in various combinations and proportions thereof. This is possible even though such drugs or their derivatives are not known or described to exert their primary therapeutic effect at the level of plasma cells, the ultimate source of antibodies. Such drugs or derivatives thereof include, but are not limited to, rituximab (Anti CD20 monoclonal antibody), belimumab, anti CD3 antibodies, anti CD19 antibody, and anti CD22 antibody, corticosteroids (e.g. Prednisolone), rapamycin, methotrexate, IVIG, cyclophosphamide, cyclosporine A, azathioprine, or mycophenolate mofetil. These additional immunomodulating agents or their derivatives include agents targeting/altering antigen presentation and/or humoral or cell mediated immune response.

In some embodiments, one or more additional immunomodulating agents can be administered concurrently with or following administration of the immune modulator. Such additional agents include, but are not limited to, folinic acid, bortezomib, high dose IVIG, rampamycin, or a B-cell targeting agent.

In some embodiments, the immune modulator is administered at a transient low-dose. The terms "transient low-dose," and "low-dose, brief-course," are used herein interchangeably to mean a dosage regimen wherein the immune modulator is administered at a lower dose (e.g., one-half, one-third, one-fourth, one-fifth, one-sixth, one-seventh, one-eighth, one-ninth, one-tenth of the dose) than it is typically administered for in the same or other applications and for a brief period of time to avoid prolonged immunosuppression.

In some embodiments, the immune modulator is methotrexate. In other embodiments, transient low-dose methotrexate is administered to a subject suffering from a metabolic disorder (e.g., a lysosomal storage disease) undergoing ERT at about one-fourth to about one-seventh of the methotrexate dose typical for cancer chemotherapy and for a period of three cycles with three days per cycle. In other embodiments, transient low-dose methotrexate is administered to a subject suffering from a metabolic disorder (e.g., a lysosomal storage disease) undergoing ERT at a daily dose of about 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg (where mg refers to mg/kg body weight).

In other embodiments, transient low-dose methotrexate is administered to a subject suffering from a metabolic disease undergoing ERT on Days 0, 1, and 2 (first cycle), Days 14, 15, and 16 (second cycle), and Days 28, 29, and 30 (third cycle). In other embodiments, transient low-dose methotrexate is administered to a subject suffering from a metabolic disease undergoing ERT on Days 0, 1, and 2 (first cycle), Days 7, 8, and 9 (second cycle), Days 14, 15, and 16 (third cycle). In other embodiments, a dose of 0.4 mg/kg body weight of methotrexate can be administered for a minimum of 3 cycles (i.e., during first three infusions of rhGAA) with 3 days of MTX/cycle resulting in a maximum daily dose of about 7 mg. In other embodiments, a dose of 0.4 mg/kg body weight of methotrexate can be administered for a total of 3 cycles (i.e., during first three infusions of rhGAA) with 3 days of MTX/cycle resulting in a maximum daily dose of about 10 mg for LOPD patients.

In other embodiments, transient low-dose methotrexate is administered to a subject suffering from a metabolic disease undergoing ERT for 3 to 5 cycles, for example, on Days 0, 1, and 2 (first cycle), Days 14, 15, and 16 (second cycle), Days 28, 29, and 30 (third cycle), Days 42, 43, and 44 (fourth cycle), and Days 56, 57, and 58 (fifth cycle) or Days 0, 1, and 2 (first cycle), Days 7, 8, and 9 (third cycle), Days 14, 15, and 16 (third cycle), Days 21, 22, and 23 (fourth cycle), and Days 28, 29, and 30 (fifth cycle). In other embodiments, a dose of 0.4 mg/kg body weight of methotrexate can be administered for a minimum of 5 cycles (i.e., during first five infusions of rhGAA) with 3 days of MTX/cycle resulting in a maximum daily dose of 7 mg. In other embodiments, a dose of 0.4 mg/kg body weight of methotrexate can be administered for a minimum of 5 cycles (i.e., during first three infusions of rhGAA) with 3 days of MTX/cycle resulting in a maximum daily dose of 10 mg for LOPD patients. In other embodiments, a cycle of immune modulator administration can consist of 3, 4, or 5 consecutive days of administration occurring every other week or every week. These embodiments are referred to as transient low-dose methotrexate (TLD-MTX) regimen.

In another embodiment, the immune modulator is administered orally about one hour before the start of ERT. In another embodiment, the immune modulator is administered subcutaneously about 15 minutes before the start of ERT.

In another embodiment, the immune modulator is formulated as a pharmaceutical composition prior to administering to a subject, according to techniques known in the art.

Another aspect of the present disclosure provides a method of reducing or preventing the formation of titers of antibodies for a therapeutic agent in a subject suffering from a metabolic disease, said method comprising administering to the subject a therapeutically effective amount of an immune modulator and the therapeutic agent such that the antibody formation is reduced or prevented.

In some embodiments, the above described methods prevent the formation of high and sustained antibody titers or the formation of sustained intermediate titers.

As used herein, the term "high and sustained antibody titer (HSAT)" refers to an antibody titer greater than or equal to about 50,000, 50,100, 50,200, 50,300, 50,400, 50,500, 50,600, 50,700, 50,800, 50,900, 51,000, 51,100, 51,200, 51,300, 51,400, 51,500, 51,600, 51,700, 51,800, 51,900, 52,000, 52,100, 52,200, 52,300, 52,400, 52,500, 52,600, 52,700, 52,800, 52,900 or 53,000 at least twice beyond 6 months on ERT. In some embodiments, HSAT refers to rhGAA IgG tiers that are greater than or equal to 51,200 at least twice beyond 6 months on ERT.

As used herein, the term "sustained intermediate titer (SIT)" refers to an antibody titer greater than or equal to about 12,000 and less than or equal to about 52,000, greater than or equal to about 12,800 and less than or equal to about 51,200, greater than or equal to about 13,600 and less than or equal to about 50,400, greater than or equal to about 14,400 and less than or equal to about 49,600, or greater than or equal to about 15,200 and less than or equal to about 48,800 within the first year of ERT. In some embodiments, SIT refers to rhGAA IgG tiers that are greater than or equal to 12,800 and less than 51,200 within the first year of ERT.

The terms, "improve," "enhance," "prevent," "preempt," or "reduce," as used herein, indicate values that are relative to a baseline measurement, such as a measurement in the same individual prior to initiation of the treatment described herein, or a measurement in a control individual (or multiple control individuals) in the absence of the treatment described herein.

The terms "treating" or "treatment" as used herein refers to both therapeutic treatment and prophylactic or preventative measures. It refers to preventing, curing, reversing, attenuating, alleviating, minimizing, suppressing, or halting the deleterious effects of a disease state, disease progression, disease causative agent (e.g., bacteria or viruses), or other abnormal condition.

The terms "effective amount" or "therapeutically effective amount" as used herein refers to an amount of a therapeutic agent sufficient to effect beneficial or desirable biological and/or clinical results. Such response may be a beneficial result, including, without limitation, amelioration, reduction, prevention, or elimination of symptoms of a disease or disorder. Therefore, the total amount of each active component of the therapeutic agent is sufficient to demonstrate a meaningful benefit in the patient, including, but not limited to, improving the efficiency of recombinant protein delivery during ERT for treatment of lysosomal storage diseases and improving the efficiency of rhGAA delivery to muscle tissues and improve the efficacy of ERT for Pompe disease. A "therapeutically effective amount" of an agent may be administered through one or more preventative or therapeutic administrations. When the term "therapeutically effective amount" is used in reference to a single agent, administered alone, the term refers to that agent alone, or a composition comprising that agent and one or more pharmaceutically acceptable carriers, excipients, adjuvants, or diluents. When applied to a combination, the term refers to combined amounts of the active agents that produce the therapeutic effect, or composition(s) comprising the agents, whether administered in combination, consecutively, or simultaneously. The exact amount required will vary from subject to subject, depending, for example, on the species, age, and general condition of the subject; the severity of the condition being treated; and the mode of administration, among other factors known and understood by one of ordinary skill in the art. An appropriate "effective" amount in any individual case may be determined by one of ordinary skill in the art. Thus, a "therapeutically effective amount" will typically fall in a relatively broad range that can be determined through routine trials.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject is a human patient that is suffering from, or at risk of developing, a lysosomal storage disease. In other embodiments, the subject is suffering from Pompe Disease. In certain embodiments, the subject is a treatment-naïve cross-reactive immunological material (CRIM)-positive Pompe disease patient. In other embodiments, the subject is a treatment-naïve cross-reactive immunological material (CRIM)-negative Pompe disease patient.

Another aspect of the present disclosure provides all that is disclosed and illustrated herein.

The following examples are offered by way of illustration and not by way of limitation.

Example 1: Study Design to Investigate Immune Tolerance Induction (ITI) with Transient Low-Dose Methotrexate Co-Initiated with ERT Treatment in IOPD and LOPD Patients To investigate immune tolerance induction (ITI) with transient low-dose methotrexate (TLD-MTX) co-initiated with recombinant human acid α-glucosidase (rhGAA), treatment-naïve cross-reactive immunologic material (CRIM)-positive infantile-onset Pompe disease (IOPD) patients were enrolled in a clinical study.

Patients and Inclusion and Exclusion Criteria

Patients with a confirmed diagnosis of IOPD (two confirmed GAA pathogenic variants) and a low GAA enzyme activity (in blood, muscle, or skin) who were CRIM-positive and ERT-naïve were enrolled in the study. CRIM status was determined by Western blot analysis and confirmed by GAA genotype or was predicted from GAA genotype alone.

Patients were classified as having classic infantile-onset Pompe disease (IOPD), atypical IOPD, or late-onset Pompe disease (LOPD). Classic IOPD was defined as age at onset ≤12 months of age with cardiomyopathy, atypical IOPD as age at onset ≤12 months of age without cardiomyopathy or >12 months to <12 years of age, and LOPD as symptom onset at >12 years of age.

Upon a new diagnosis of Pompe disease, the detailed protocol was shared with the patient's local treating physician, including the dosing schedule of methotrexate, IgG antibody monitoring guidelines, and laboratory analyses for safety measures. Follow-up data from the local treating team were requested every 3 months.

Previously described methods were used for determining CRIM status, (Bali et al. (2012) *Am. J. Med. Genet. C. Semin. Med. Genet.* 160C:40-49; Berrier et al. (2015) *Genet.*

Med. 17:912-18) GAA pathogenic variants, and anti-rhGAA IgG antibody titers. (Kishnani et al. (2006) *J. Pediatr.* 149:89-97).

Ethical Approval and Parent, Guardian, or Adult Patient Consent

All patients were enrolled in an Institutional Review Board (IRB)-approved study. Nineteen patients were enrolled in a Duke IRB (Hock Plaza, Suite 405, 2424 Erwin Road, Campus Box #2712, Durham, NC 27705, USA)-approved protocol 00001562 (LDN6709 Site 206; Clinical-Trials.gov NCT01665326; Determination of Cross-Reactive Immunological Material (CRIM) Status and Longitudinal Follow-up of Individuals with Pompe disease). One patient was enrolled in an IRB-approved study at an institution local to the patient (Shaare Zedek Medical Center, Jerusalem, Israel). Informed consent was obtained by telephone from minor patients' parent(s) or legal guardian(s) for determination of CRIM status and long-term follow-up of each patient. The patient's local physician was a third-party witness to the verbal telephone consent. The consent form was then signed by the parent(s)/legal guardian(s) and returned via email or fax to the Duke study staff member for his/her signature. A copy of the fully signed consent form was returned to the parent(s)/legal guardian(s).

Study Design

The study timeline for ERT and methotrexate dosing is shown in FIG. 1. Patients received intravenous (IV) infusions of ERT at 20 mg/kg body weight every other week (EOW) based on the package insert or on a different regimen based on decision of the treating clinician.

No premedication was considered necessary for ERT infusion, unless a patient began to experience infusion-associated reactions (IARs). If an IAR occurred, patients were treated symptomatically once anti-rhGAA immunoglobulin E (IgE) status was determined, so as not to mask any possible hypersensitivity reaction or anaphylactic response. The potential side effects of alglucosidase alfa include anaphylaxis and allergic reactions. Pre-medications for methotrexate administration included oral acetaminophen and oral or intravenous ondansetron.

Methotrexate at 0.4 mg/kg body weight was administered subcutaneously (or orally if subcutaneous administration was not possible) on three consecutive days/MTX cycle/infusion; with the first three ERT infusions (i.e., on Days 0, 14, and 28 for patients infused EOW) for a total of 3 cycles. On the day of ERT infusion, methotrexate was administered 15 minutes (if subcutaneous) or 1 hour (if oral) before infusion initiation and again on the following 2 days. To exemplify the schedule, in a patient receiving ERT infusion EOW, methotrexate was administered on Days 0, 1, and 2 (first cycle); Days 14, 15, and 16 (second cycle), and Days 28, 29, and 30 (third cycle). As stated earlier, the dose and frequency of ERT could be increased at the discretion of the treating physician, based on patients' clinical and IAR status, in which case methotrexate cycles were adjusted accordingly (see FIG. 2 for details).

Methotrexate adjustments were not made for high white blood cell counts. The methotrexate dose was withheld if the absolute neutrophil count (ANC) was <750/mm$^3$ or liver function tests (aspartate aminotransferase [AST] and alanine aminotransferase [ALT]) were >3 times their respective baseline values. Folinic acid supplementation, although not directed in the protocol, could be given at the treating physician's discretion if there was a concern with methotrexate toxicity.

Immune Response

Anti-rhGAA IgG antibodies were determined by Sanofi Genzyme (Framingham, MA, USA) using enzyme-linked immunosorbent assays and confirmed using radioimmunoprecipitation as described previously (Kishnani et al. (2006) *J. Pediatr.* 149:89-97). Antibody analyses were recommended to be performed at Days −1, 28, 56, 84, 112, 140, 168, 196, 224, 252, 280, 308, 336, and 364.

Hematologic and Biochemical Analyses

Figure 2:
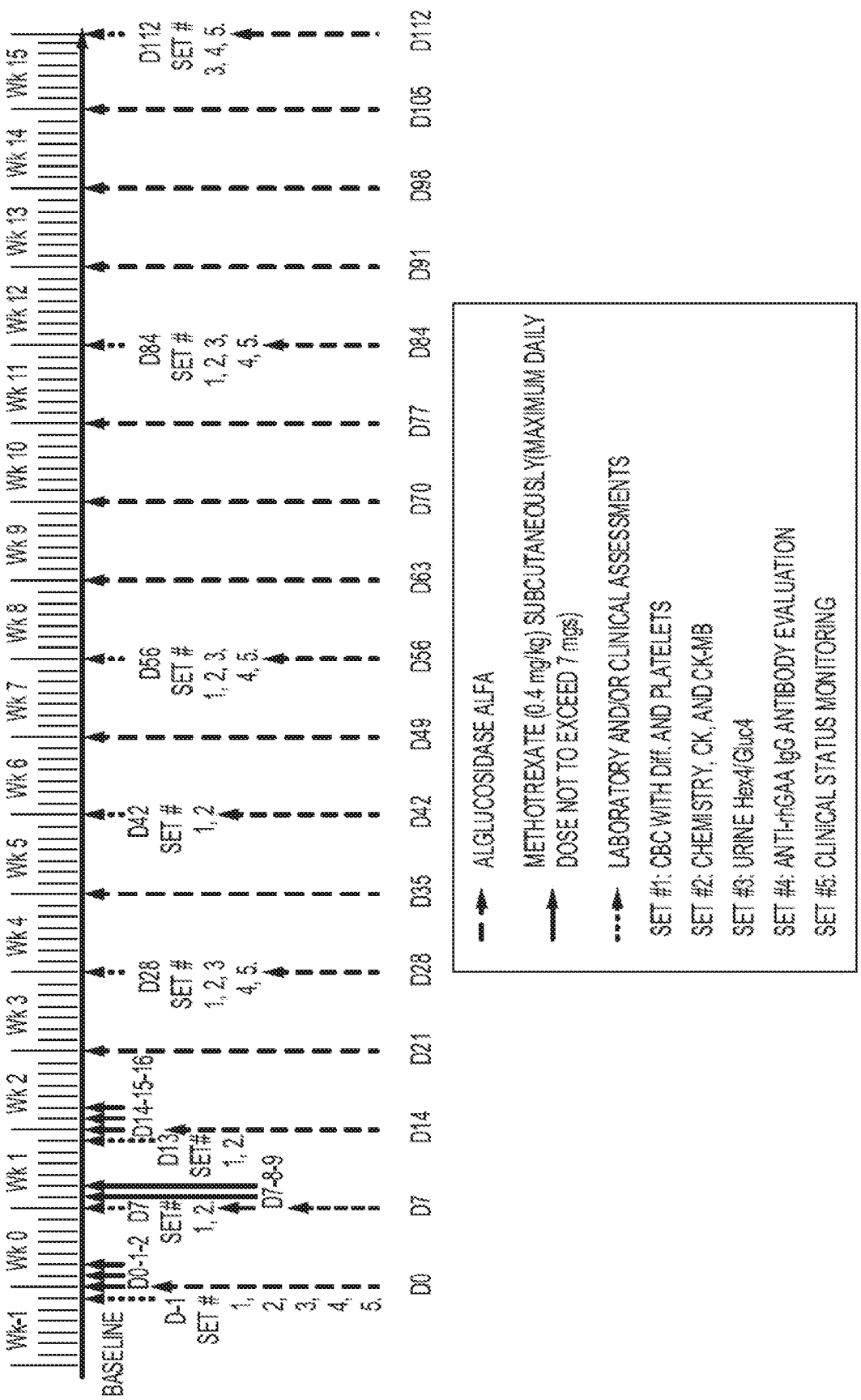
FIG. 2 is a schematic showing the study timeline for infantile Pompe disease patients receiving weekly ERT infusions.
Figure 3A:
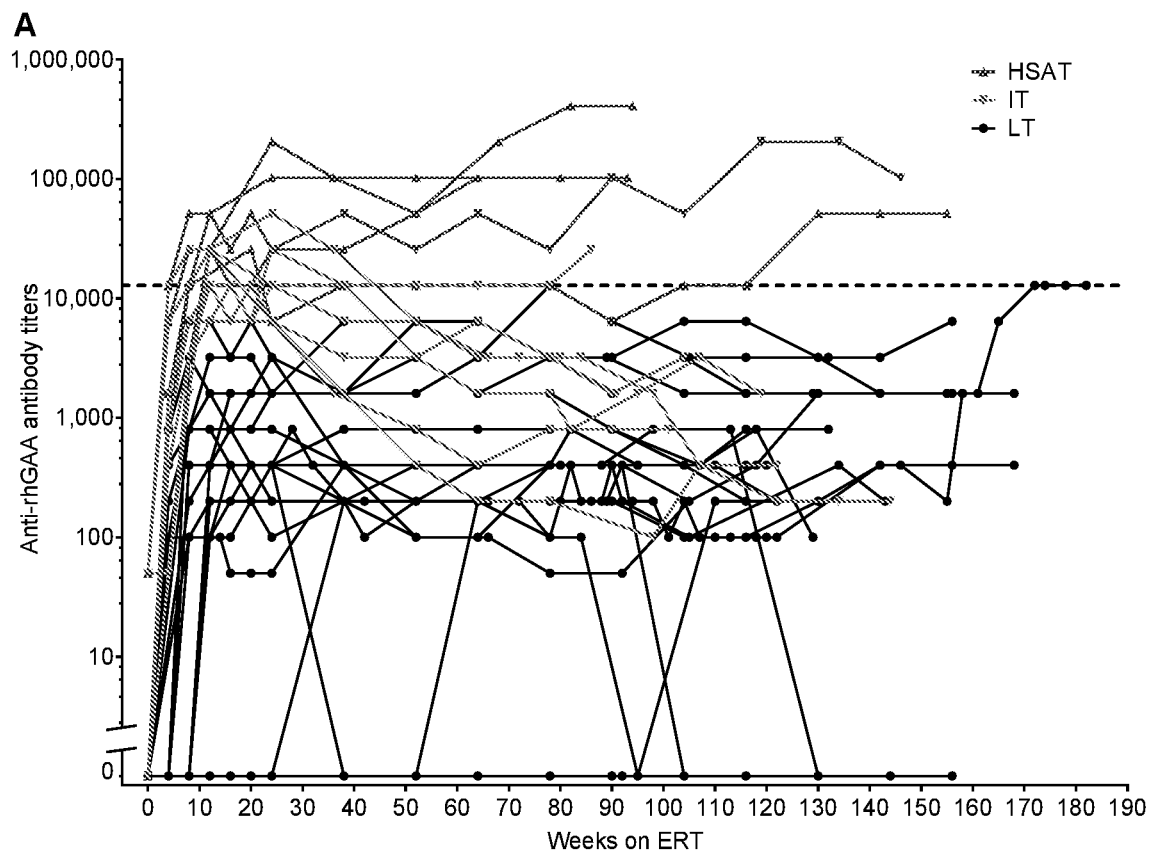
FIG. 3A-3D are graphs showing the immune response over time in a comparator group of 37 CRIM-positive IOPD patients.
Figure 3B:
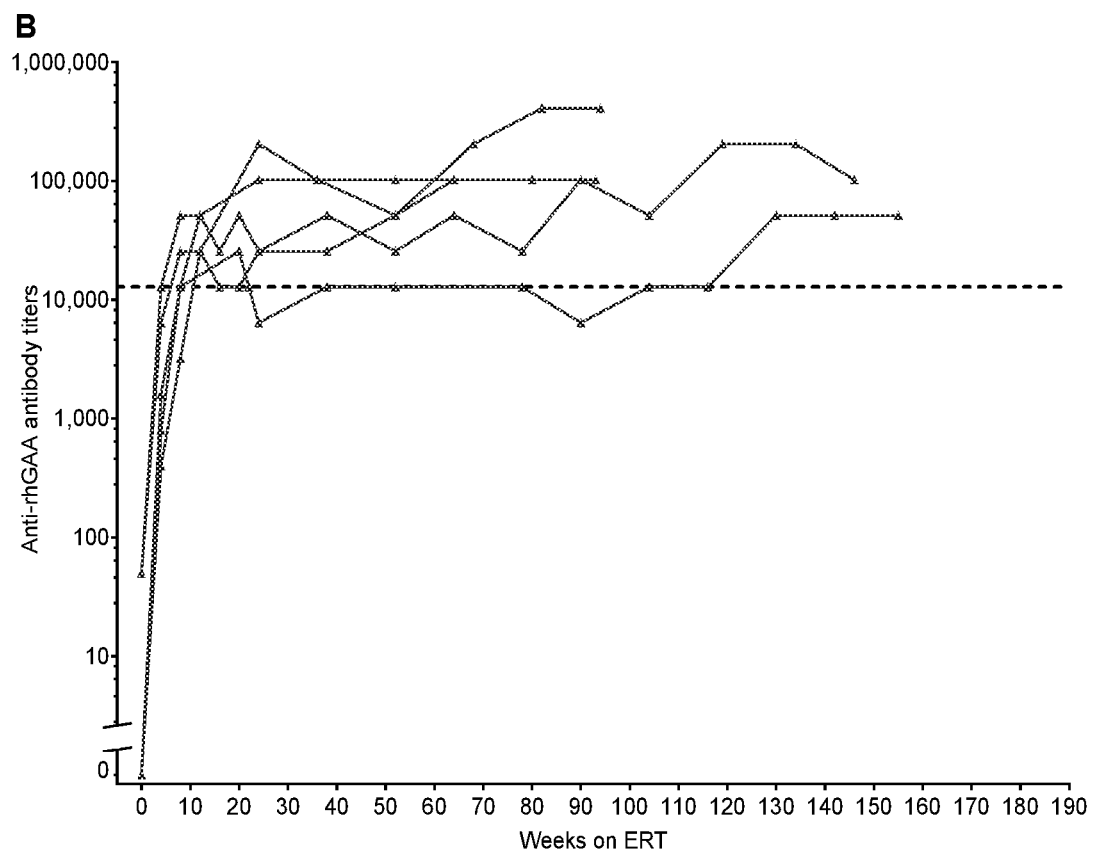
Figure 3C:
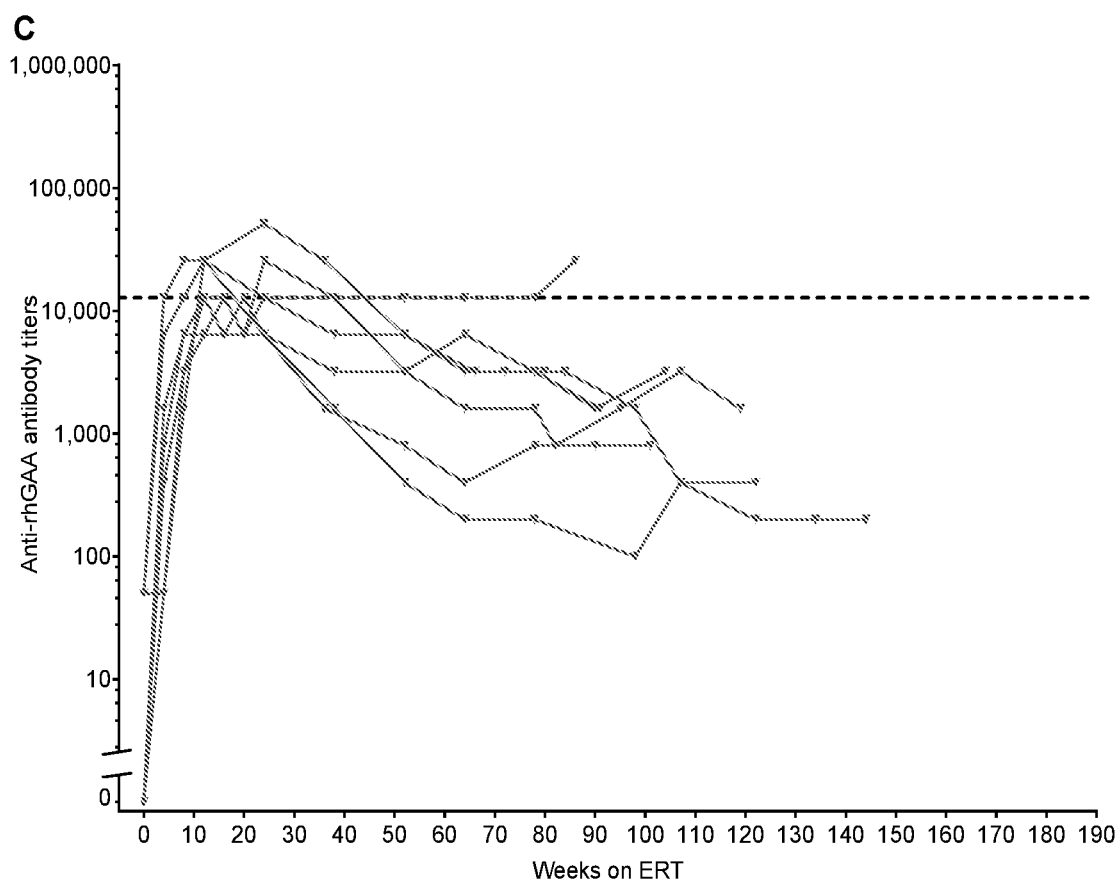
Figure 3D:
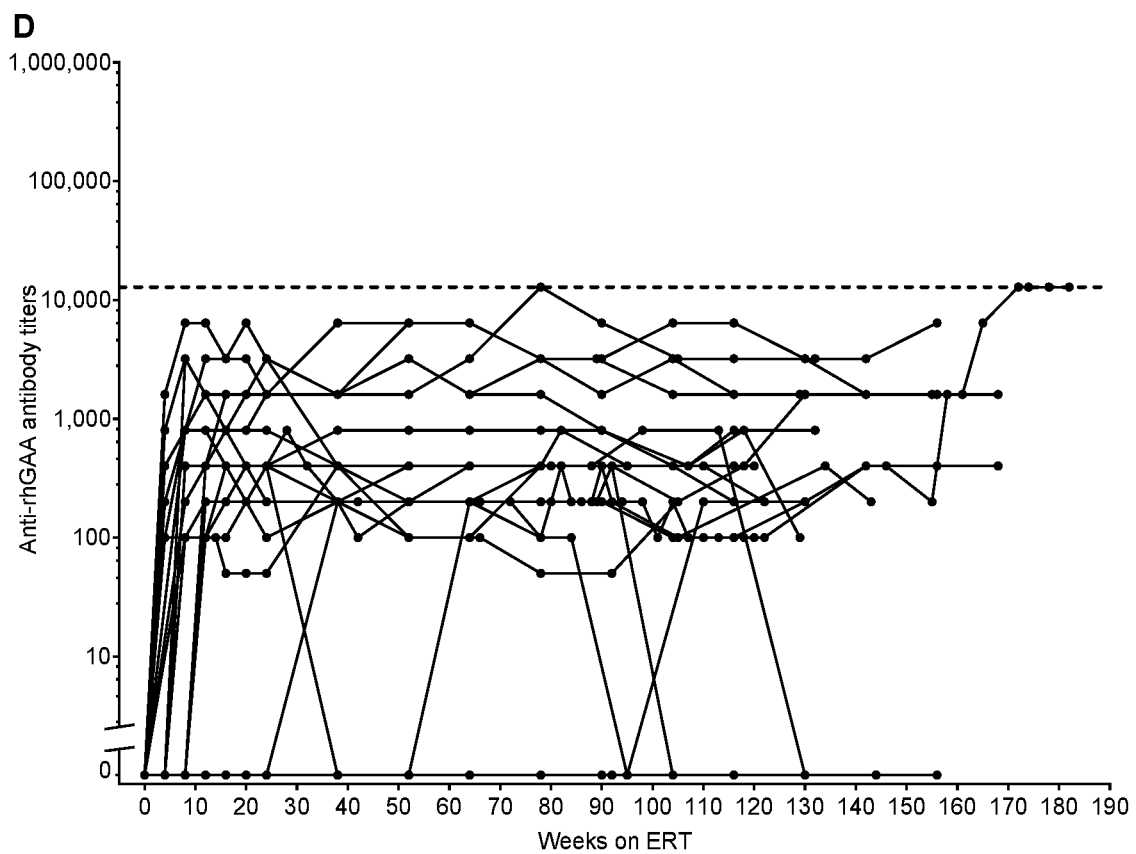

On Days −1 (baseline), 13, 28, 42, 56, 84, 168, 252, 336, and 364, blood samples were recommended to be collected for hematologic and biochemical analyses for patients receiving ERT EOW. The sampling schedule was modified for patients receiving ERT weekly (FIG. 2). Complete and differential blood counts and platelets were evaluated and monitored for platelet counts <50,000/mm$^3$, ANC <750/mm$^3$, and treatment-resistant infections. Biochemical analyses monitored alanine aminotransferase (ALT), aspartate aminotransferase (AST), creatine kinase (CK), and CK-MB levels. Post-treatment increases in AST and ALT levels were noted if exceeding three times their respective baseline levels. Urine samples for the glucose tetrasaccharide (Glc$_4$) biomarker were collected on Days: −1, 28, 56, 84, 112, 140, 168, 196, 224, 252, 280, 308, 336, and 364.

Statistical Analysis rhGAA IgG titers were determined over time. Patients were classified into HSAT (≥51,200 on ≥2 occasions at or beyond 6 months on ERT), sustained intermediate titer (SIT) (≥12,800 and <51,200 within the first year of ERT), and low titer (LT; ≤6,400 within the first year of ERT) groups based on the longitudinal anti-rhGAA IgG titers. The lower bound of SIT, ≥12,800, was associated with increase in ERT clearance in a pharmacokinetic study reported in the alglucosidase alfa prescribing information; the upper bound of LT, ≤6,400, was 1 dilution level below this. Medians and ranges were determined for baseline, peak, and last titers, although our focus was on longitudinal titers through time because sustained titers affect clinical response.

Comparator Group for CRIM-Positive IOPD

A retrospective chart review of 37 CRIM-positive patients with IOPD was conducted from the original rhGAA clinical trials, including patients on ERT for ≥6 months who did not receive immunomodulation. The comparators received rhGAA alone. The GAA variant data and age at ERT initiation were compared with our cohort of TLD-MTX recipients. Immune responses over time were classified into HSAT, SIT, and LT as defined above, and time to seroconversion, peak titers, titers at Weeks 12, 24, and 52 were compared with our present cohort of TLD-MTX recipients.

The summary immunogenicity data previously published for naïve alglucosidase alfa recipients with LOPD in the Late-Onset Treatment Study was referred to for comparison with the LOPD patients.

Example 2: Study Results of ITI with Transient Low-Dose Methotrexate Co-Initiated with ERT Treatment in CRIM-Positive and CRIM-Negative IOPD and LOPD Patients To investigate immune tolerance induction (ITI) with transient low-dose methotrexate (TLD-MTX) co-initiated with recombinant human acid α-glucosidase (rhGAA), a cohort of 17 newly-diagnoses, treatment-naïve cross-reactive CRIM-positive patients with Pompe disease were treated.

Patient Disposition

There were 17 CRIM-positive patients with Pompe disease, naïve to alglucosidase alfa, who received methotrexate ITI; 15 patients with IOPD (IOPD, n=10; atypical IOPD, n=5) and 2 patients with LOPD.

Longitudinal follow-up data of >6 months were available for 17 patients. Those with IOPD (n=10) had a follow-up range of 42-122 weeks, those with atypical IOPD (n=5) had a follow-up range of 58-145 weeks, and the 2 patients with LOPD had follow-up of 27 weeks and 63 weeks, respectively. Baseline demographics of the 17 patients with >6 months' follow-up are presented in Table 1.

TABLE 1

Baseline demographic characteristics of IOPD and LOPD patients that received TLD-MTX protocol

| Patient | Sex | GAA pathogenic variants Variant 1 | GAA pathogenic variants Variant 2 | Age at start of ERT | ERT done and frequency | Protocol deviation |
|---|---|---|---|---|---|---|
| IOPD1 | Male | c.953T > C Missense p.Met318Thr | c.1292_1295dupTGCA Duplication, frameshift, truncation p.Gln433A1afsX74 | 0.9 months | 20 mg/kg weekly | Only 1 dose of methotrexate administered in the 2nd cycle due to ANC <750. Methotrexate administered SC for each dose |
| IOPD2 | Male | c.1004G > A Missense p.Gly335Glu | c.1841C > A Missense p.Thr614Lys | 3.3 months | 20 mg/kg biweekly | No deviations |
| IOPD3 | Male | c.1118T > G Missense p.Leu373Arg | c.1118T > G Missense p.Leu373Arg | 4.0 months | 20 mg/kg biweekly | 1st cycle: 3 methotrexate doses; 2nd and 3rd cycles: 1 methotrexate dose each; 4th cycle: 3 methotrexate doses. Methotrexate administered SC |
| IOPD4 | Female | c.2560C > T Nonsense p.Arg854X | c.1466A > G Missense p.Asp489Gly | 0.8 months | 20 mg/kg biweekly | 3rd cycle of methotrexate and alglucosidase alfa administered on Week 5, due to illness during Week 4. Methotrexate administered SC for all doses |
| IOPD5 | Female | c.665T > G p.Val222Gly | c.1437 + 2T > C Deletion p.Asp443_Lys479del | 3.5 months | 20 mg/kg weekly | No deviations. Methotrexate administered SC |
| IOPD6 | Female | c.1114C > T Missense p.His372Tyr | c.1979G > A Missense p.Arg660His | 11.2 months | 20 mg/kg biweekly | No deviations. Methotrexate administered PO |
| IOPD7 | Female | c.2456G > C Missense p.Arg819Pro | c.2456G > C Missense p.Arg819Pro | 1.2 months | 20 mg/kg biweekly | No deviations. Methotrexate administered SC |
| IOPD8 | Female | c.525delT Frameshift p.Glu176Argfs*45 | c.2297A > C Missense p.Y766S | 4.6 months | 20 mg/kg biweekly | 3rd cycle of methotrexate and alglucosidase alfa administered on Week 5, due to rhinovirus infection during Week 3 Methotrexate administered SC |
| IOPD9** | Female | c.1A > G Initiator codon variant | c.1A > G Initiator codon variant | 12.9 months | 20 mg/kg biweekly | No deviations. Methotrexate administered SC |
| IOPD10 | Female | c.1942G > A p.Gly648Ser | c.1942G > A p.Gly648Ser | 1.7 months | 20 mg/kg biweekly | 3rd dose of 3rd cycle of methotrexate was not administered due to fever. Methotrexate administered SC |
| AIOPD1 (IOPD11) | Female | c.1447G > A Missense p.Gly483Arg | c.2560C > T Truncation p.Arg854X | 13.5 months | 20 mg/kg biweekly | No deviations. 3rd methotrexate dose of 3rd cycle was given PO, all others given SC |
| AIOPD2 | Male | Splice variant in exon 10 | Splice Variant in exon 10 | 128.3 months | 20 mg/kg biweekly | None. Methotrexate administered PO |

TABLE 1-continued

Baseline demographic characteristics of IOPD and LOPD patients that received TLD-MTX protocol

| Patient | Sex | GAA pathogenic variants | | Age at start of ERT | ERT done and frequency | Protocol deviation |
|---|---|---|---|---|---|---|
| | | Variant 1 | Variant 2 | | | |
| AIOPD3 | Male | c.-32-13 T > G Splice variant r.spl | c.743T > C Missense p.Leu248Pro | 21.3 months | 20 mg/kg biweekly | For all 3 cycles of methotrexate 1st dose: SC; 2nd dose: PO; 3rd dose: PO |
| AIOPD4 | Male | Missense p.Leu355Pro | Missense p.Leu355Pro | 72.2 months | 20 mg/kg biweekly | No deviations. Methotrexate administered SC |
| AIOPD5 (IOPD12) | Male | c.1A > G Initiator codon variant | c.2234T > C p.Leu355Pro | 0.7 months | 20 mg/kg biweekly | No deviations. Methotrexate administered SC |
| IOPD13 | Female | c.1979G > A p.Arg660His | c.2560C > T p.Arg854X | 4.5 months | 20 mg/kg EOW*** | No deviations. Methotrexate administered SC |
| IOPD14 | Female | c.525delT p.Glu176Argfs*45 | c.1979G > A p.Arg660His | 4.0 months | 20 mg/kg EOW | MTX administered PO 1$^{st}$ MTX dose of 3$^{rd}$ cycle was skipped |
| LOPD1 | Male | c.-32-13T > G Splice variant | c.1438-1G > C Splice variant | 10 years | 20 mg/kg biweekly | For all 3 cycles of methotrexate 1st dose: SC; 2nd dose: PO; 3rd dose: PO |
| LOPD2 | Male | c.-32-13T > G Splice variant | c.877G > A Missense p.Gly293Arg | 62.8 years | 20 mg/kg biweekly | No deviations. Methotrexate administered PO |

TLD-MTX, transient low-dose methotrexate,
ANC, absolute neutrophil count;
IOPD, infantile-onset Pompe disease;
EOW, every other week;
PO, orally (per os);
SC, subcutaneous.
*ERT dose and frequency was determined based on the clinical judgement of the treating physician.
**Patient IOPD9 is CRIM-negative.
***ERT dose was changed to 40 mg/kg/weekly after two infusions.
ANC, absolute neutrophil count;
IOPD, infantile-onset Pompe disease;
LOPD, late-onset Pompe disease;
PO, orally (per os);
SC, subcutaneous.

Immune Response—Comparators

Five (13.5%), 7 (18.9%), and 25 (67.6%) of the 37 comparator CIOPD patients developed HSAT, SIT, and LT, respectively. All HSAT patients seroconverted by 4 weeks; for the SIT and LT patients, median time to seroconversion was 4 weeks (4-8 weeks, n=7) and 8 weeks (4-64 weeks, n=23), respectively; 2 patients did not seroconvert. Group median peak titers were 204,800 (range, 51,200-409,600) for HSAT, 25,600 (range, 12,800-51,200) for SIT, and 800 (range, 200-12,800) for LT. Group median last titers (at median times on alglucosidase alfa) were 102,400 for HSAT (Week 94) (range, 51,200-409,600), 1,600 for SIT (Week 104), and 400 for LT (Week 130; individual data are shown in FIG. 3A-3D). These data were used for comparison with the present methotrexate-treated IOPD patients (FIG. 4A).

Immune Response—Methotrexate Recipients

Figure 4A:
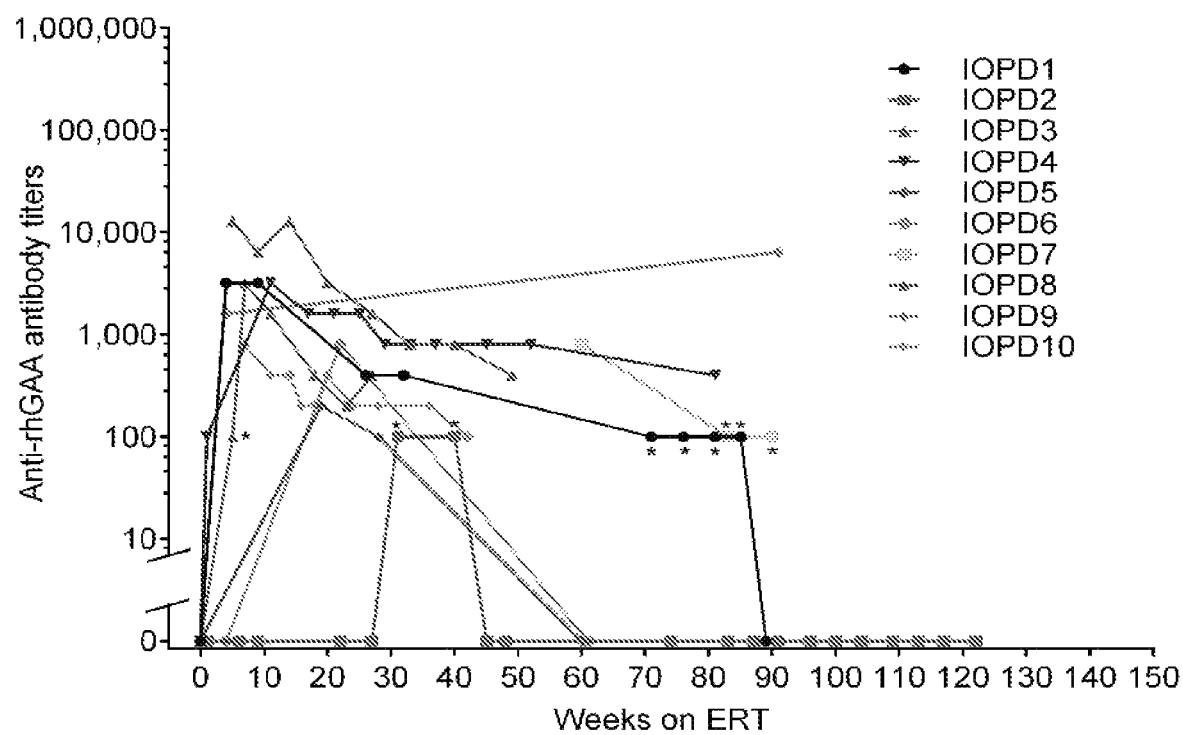
FIG. 4A-4C are graphs showing the immune response in all patients with Pompe disease who received low-dose methotrexate.
Figure 4B:
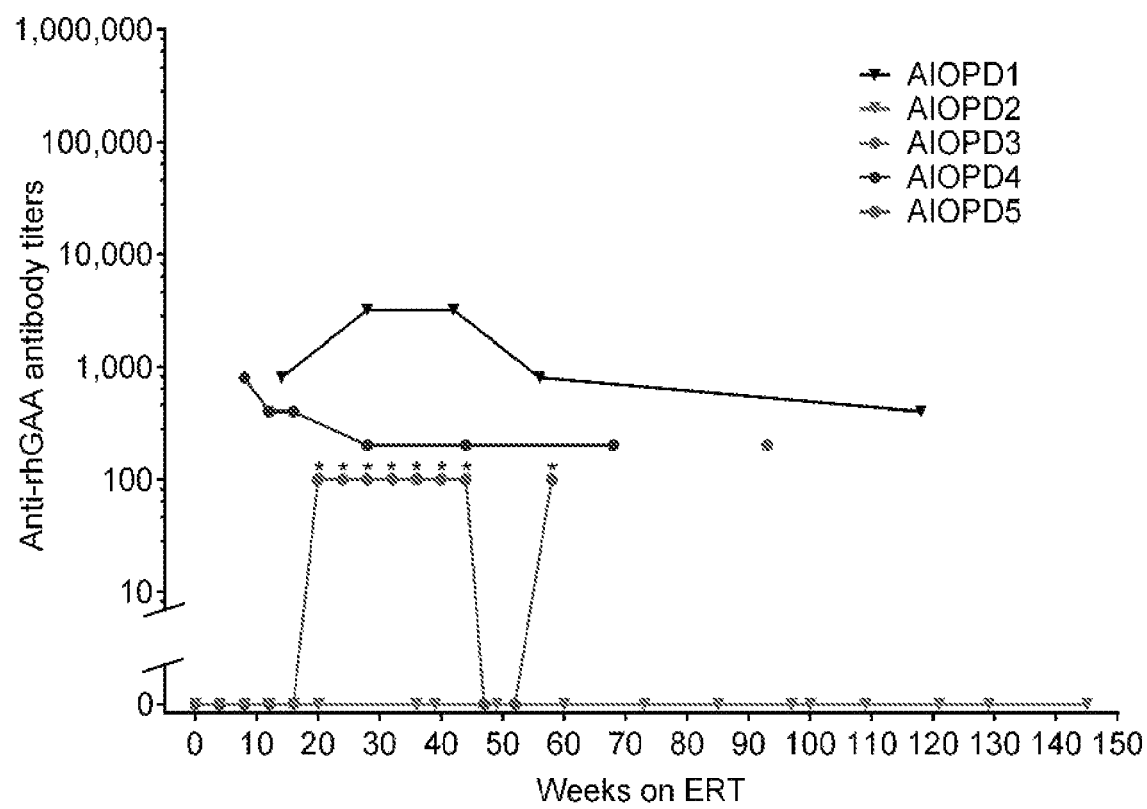
Figure 4C:
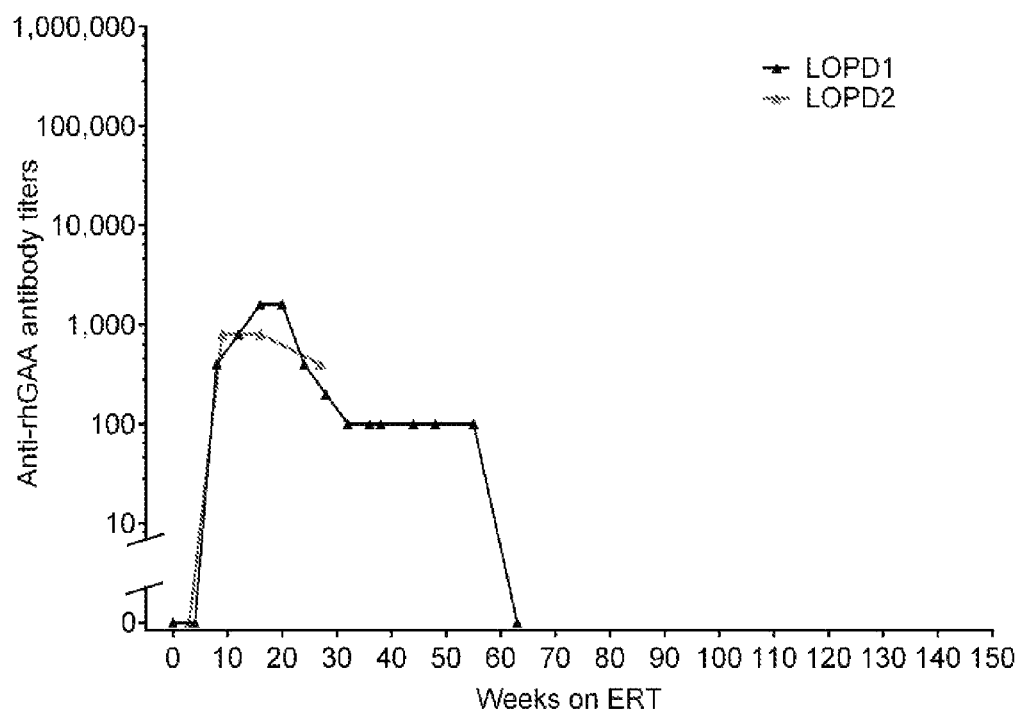

The immune response for each methotrexate-treated patient over time is shown by disease state subsets in FIG. 4A-4C, and summarized in Table 2. The median last titer was 100 (range, 0-6400) and the median time on alglucosidase alfa was ~68 weeks (range, 27-145 weeks). Only 1 patient, who was in the IOPD group, had titers of 12,800 (twice at Weeks 4 and 12) and had received only a single dose of methotrexate in cycles 2 and 3 instead of 3 doses per cycle. This patient, had the highest titer observed in the study; other methotrexate recipients remained LT. One patient never seroconverted, and 2 additional patients had titers remaining <100 (seropositive on screening assay, but below the limit of titer measurement). No patients who received methotrexate developed HSAT.

TABLE 2

Immune response for patients who had >6 months follow-up

| Patient | Peak antibody titer since immune tolerance induction | Time on ERT therapy (peak titer), weeks | Last antibody titer | Time on ERT therapy (last titer), weeks |
|---|---|---|---|---|
| IOPD | | | | |
| IOPD1 | 3,200 | 4 | 0 | 89 |
| IOPD2 | <100 | 31 | 0 | 122 |
| IOPD3 | 12,800* | 4 | 400 | 49 |
| IOPD4 | 3,200 | 12 | 400 | 81 |
| IOPD5 | 200 | 20 | 0 | 60 |
| IOPD6 | 800 | 22 | 0 | 61 |

TABLE 2-continued

Immune response for patients who had >6 months follow-up

| Patient | Peak antibody titer since immune tolerance induction | Time on ERT therapy (peak titer), weeks | Last antibody titer | Time on ERT therapy (last titer), weeks |
|---|---|---|---|---|
| IOPD7 | 800 | 60 | <100 | 90 |
| IOPD8 | 3,200 | 7 | 100 | 49 |
| IOPD9 | 6,400 | 91 | 6,400 | 91 |
| IOPD10 | 800 | 7 | 100 | 42 |
| Atypical IOPD | | | | |
| AIOPD1 (IOPD11) | 3,200 | 28 | 400 | 118 |
| AIOPD2 | Never seroconverted | N/A | 0 | 145 |
| AIOPD3 | <100 | 20 | <100 | 58 |
| AIOPD4 | 800 | 8 | 200 | 68 |
| AIOPD5 (IOPD12) | 200 | 93 | 200 | 93 |
| LOPD | | | | |
| LOPD1 | 1,600 | 16 | 0 | 63 |
| LOPD2 | 800 | 9 | 400 | 27 |

IOPD, infantile-onset Pompe disease;
LOPD, late-onset Pompe disease.
*Patient IOPD3 only received a single dose of methotrexate in cycles 2 and 3 instead of 3 doses.

Safety—Hematologic and Biochemical Analyses

Data for measures of ANC, AST, and ALT are summarized in Table 3. Two IOPD patients developed ANC <750 cells/mm$^3$; 1 IOPD patient had missing ANC data. One IOPD patient developed both AST >3× baseline and ALT >3× baseline, a further two developed ALT >3× baseline, and 2 had missing AST and ALT data. None of the atypical or LOPD patients developed ANC <750 cells/mm$^3$ or AST and ALT >3× baseline levels.

TABLE 3

ANC, AST, and ALT for the first 6 weeks on alglucosidase alfa

| Patient | ANC < 750 cells/mm$^3$ (Yes/No) | AST > 3x baseline (Yes/No) | ALT > 3x baseline (Yes/No) |
|---|---|---|---|
| IOPD | | | |
| IOPD1 | Yes | No | No |
| IOPD2 | No | Baseline value not available | Baseline value not available |
| IOPD3 | Yes | No | Yes |
| IOPD4 | No | No | No |
| IOPD5 | No | Yes | Yes |
| IOPD6 | No | No | Yes |
| IOPD7 | Not available | Not available | Not available |
| IOPD8 | No | No | No |
| IOPD9 | No | No | No |
| IOPD10 | No | No | No |
| Atypical IOPD | | | |
| AIOPD1 (IOPD11) | No | No | No |
| AIOPD2 | No | No | No |
| AIOPD3 | No | No | No |
| AIOPD4 | No | No | No |
| AIOPD5 (IOPD12) | No | No | No |
| LOPD | | | |
| LOPD1 | No | No | No |
| LOPD2 | No | No | No |

ALT, alanine aminotransferase;
ANC, absolute neutrophil count;
AST, aspartate aminotransferase;
IOPD, infantile onset Pompe disease;
LOPD, late-onset Pompe disease.

Discussion

Brief-course, low-dose, single-drug methotrexate administered concurrently with rhGAA initiation to treatment-naïve CRIM-positive patients with Pompe disease (predominantly IOPD or atypical IOPD) resulted in 1 of 17 patients remaining seronegative and 2 more patients retaining titers <100. The cohort's median last titer was 100 (range 0-6400) at a median time of 68 weeks (range, 27-145 weeks) of alglucosidase alfa therapy. No methotrexate recipients developed HSAT. The highest observed titer was 12,800 at Weeks 5 and 14 in an IOPD patient (Patient 3), whose methotrexate cycles 2 and 3 had consisted of one dose each; by Week 20 the patient's titer decreased to 3200 and further to 400 at Week 49. All other methotrexate recipients remained LT throughout, contrasted to 5/37 HSAT (peak 51,200-409,600), 7/37 IT (12,800-51,000), and 23/37 LT (200-12,800) among IOPD comparators.

The two methotrexate-treated LOPD patients remained LT, with lower peak and sustained antibody titers than the median peak in the LOTS publication (6,400 at a median time of 12 weeks of alglucosidase alfa therapy, declining to a median last titer of 1,600 at Week 78) and also remained lower than the LOTS geometric mean titers (maximum 2,925 at Week 44; last 1,607 at Week 78). LOTS peak IgG titer quartiles (supplementary online data) were 200-1,600 (n=17), 3,200 (n=12), 6,400-12,800 (n=16), and 25,600-819,200 (n=14). One methotrexate-treated LOPD patient in this study had a maximal titer of 1,600 (Weeks 16 and 20), decreasing to 100 (Weeks 32-55), and then to 0 (Week 63). The other LOPD patient had an LT maximal titer of 800 (Weeks 9-16), decreasing to 400 thereafter (Week 27).

In a German case series of 10 LOPD patients on alglucosidase alfa for 4 years with annual antibody titers, 1 remained seronegative, 1 had a titer of 0 at every timepoint, except Year 2, and 1 remained at <100 throughout; 4 more had no titers >3,200 at any timepoint. Two patients had titers never <12,800, peaking at 25,600 and remaining at 12,800 at Year 4. No patients exceeded 25,600.

It appears, based on expectations from historical data, that low-dose methotrexate successfully induced immune tolerance in this cohort of patients.

No serious AEs were related to methotrexate. No patients discontinued the protocol for safety reasons. Some had methotrexate doses postponed because of their clinical status. Two of 9 IOPD patients with ANC data (22%) and no atypical IOPD or LOPD patients experienced neutropenia (ANC <750 cells/mm$^3$), which was transient, and ANC returned to normal levels. Overall, patients tolerated the methotrexate protocol reasonably.

Example 3: Study Results of ITI with Transient Low-Dose Methotrexate Co-Initiated with ERT Treatment in CRIM-Positive and CRIM-Negative IOPD Patients To investigate immune tolerance induction (ITI) with transient low-dose methotrexate (TLD-MTX) co-initiated with recombinant human acid α-glucosidase (rhGAA), a cohort of 14 newly-diagnosed, treatment-naïve Pompe patients were treated.

Patient Disposition

The data reported above in Example 2 for patient IDs IOPD1-IOPD10, AIODP1 (referred to in Example 3 as IOPD11) and AIOPD5 (referred to in Example 3 as IOPD12) were combined and further analyzed with two additional Pompe patients, IOPD13 and IOPD14. Fourteen ERT-naïve patients with Pompe disease received prophylactic methotrexate ITI at the median age of 3.8 months (range, 0.7-13.5 months). Longitudinal follow-up data of >6 months were available for 14 patients with IOPD (13 CRIM-positive patients and 1 CRIM-negative patient). Of the 28 total GAA variants in the TLD-MTX group, 18 (64.3%), 3 (10.7%), 3 (10.7%), 3 (10.7%), and 1 (3.6%) were missense, frameshift, initiator codon, nonsense, and splice site variants, respectively. The patients' baseline demographics are presented in Table 1. The CRIM-negative patient (IOPD9) who received TLD-MTX protocol is an international patient initially thought to be CRIM-positive. No patients in this cohort were diagnosed via newborn screening.

ERT-Monotherapy Treated CRIM-Positive Patients (Comparator Group)

Figure 5:
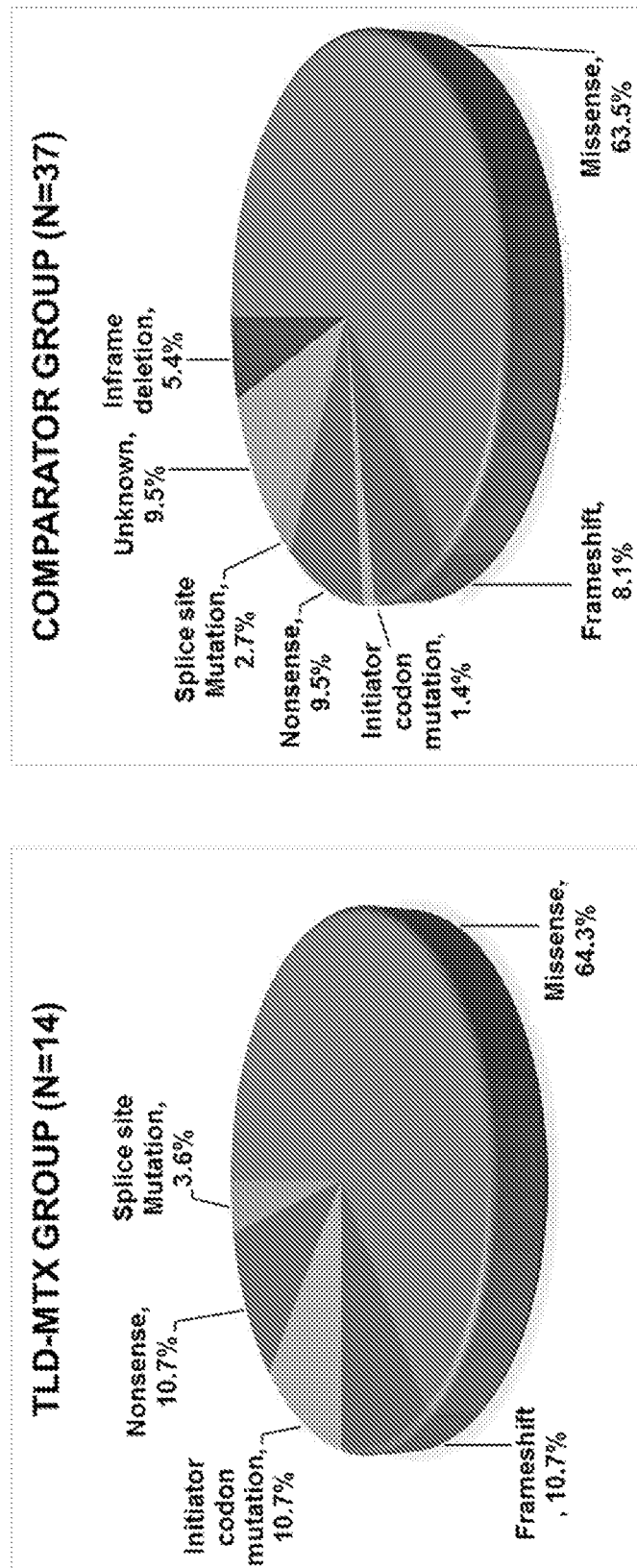
FIG. 5 provides pie charts showing the comparison of GAA variants in IOPD patients treated with TLD-MTX with CRIM-positive IOPD patients treated with ERT monotherapy.
Figure 6:
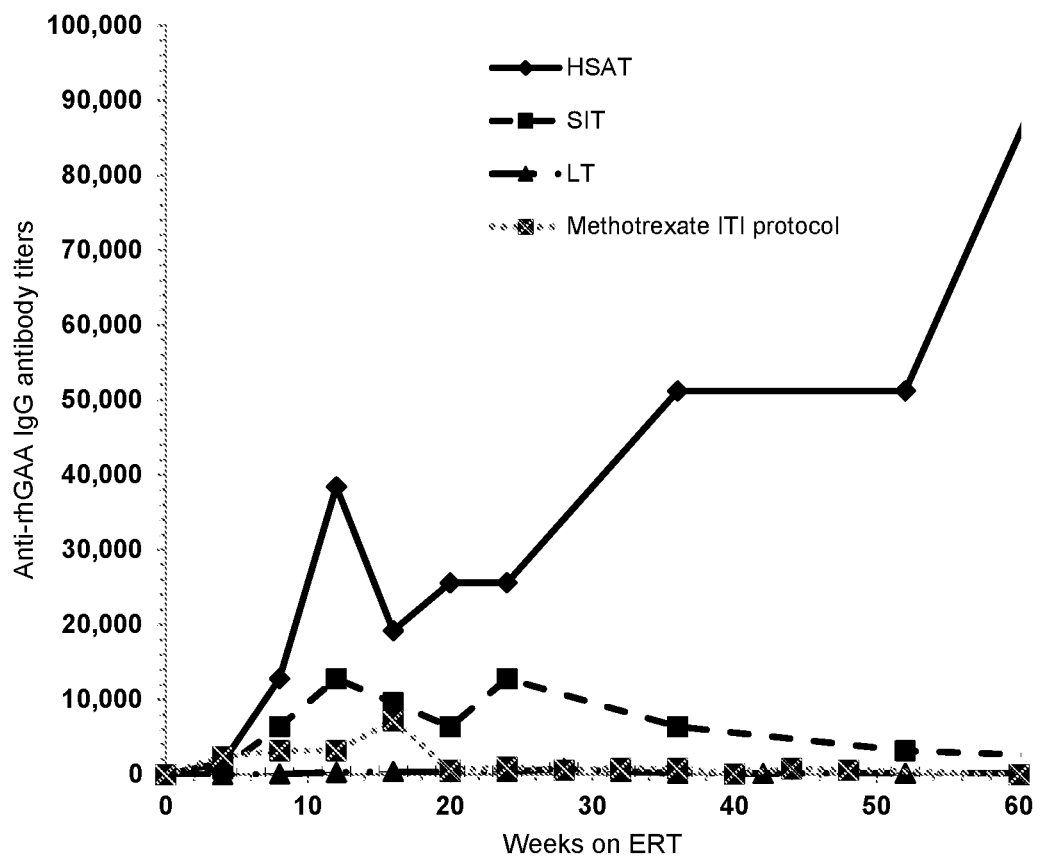
FIG. 6 is a graph showing a comparison of longitudinal IgG antibody titers in IOPD patients treated with TLD-MTX with CRIM-positive IOPD patients treated with ERT monotherapy.

Thirty-seven CRIM-positive patients were identified who received ERT-monotherapy at a median age of 6.9 months (range, 0.5-43.1 months). Age at ERT start was later in ERT-monotherapy group (median, 6.9 months) as compared with TLD-MTX group (median, 3.8 months). Of the 74 total GAA variants in the ERT monotherapy group, 47 (63.5%), 6 (8.1%), 1 (1.4%), 7 (9.5%), 2 (2.7%), 7 (9.5%), and 4 (5.4%) were missense, frameshift, initiator codon, nonsense, splice site, unknown, and in-frame deletion variants, respectively. The GAA variant data in the CRIM-positive patients in the comparator group (ERT-monotherapy) were similar to those in the TLD-MTX group (FIG. 5).

Five (13.5%), 7 (18.9%), and 25 (67.6%) of the 37 IOPD monotherapy patients developed HSAT, SIT, and LT, respectively; thus, 32.4% developed SIT or HSAT overall. All HSAT patients seroconverted by 4 weeks; for the SIT and LT patients, median time to seroconversion was 4 weeks (4-8 weeks, n=7) and 8 weeks (4-64 weeks, n=23), respectively; 2 patients did not seroconvert. Group median peak titers were: 204,800 (range, 51,200-409,600) for HSAT (median time of peak, Week 82); 25,600 (range, 12,800-51,200) for SIT (Week 12); and 800 (range, 200-12,800) for LT (Week 38). Group median last titers (at group median times on ERT) were: 102,400 for HSAT (Week 94) (range, 51,200-409,600); 1,600 for SIT (Week 104) (range, 200-25,600); and 400 for LT (Week 130) (range, 0-12,800); individual data are shown in FIG. 3A-3D. These data were used for comparison with the present TLD-MTX-treated IOPD patients (FIG. 6 and FIG. 3A-3D). Comparison of median anti-rhGAA IgG antibody titers at Weeks 12, 24, and 52, and median peak titers is shown in Table 4.

TABLE 4

Comparison of longitudinal immune response between ERT monotherapy and TLD-MTX groups*

| Groups | HSAT | SIT | LT |
|---|---|---|---|
| CRIM-positive IOPD on ERT monotherapy (n = 37) | | | |
| Percent | 13.5% (n = 5) | 18.9% (n = 7) | 67.6% (n = 25) |
| Median titers (Week 12) | 25,600 (range: 12,800-51,200) | 12,800 (range: 6,400-25,600) | 400 (range: 0-6,400) |
| Median titers (Week 24) | 25,600 (range: 6,400-204,800) | 12,800 (range: 6,400-51,200) | 400 (range: 0-3,200) |
| Median titers (Week 52) | 51,200 (range: 12,800-102,400) | 3,200 (range: 400-12,800) | 200 (range: 0-6,400) |
| Median peak titers | 204,800 (range: 51,200-409,600) | 25,600 (range: 12,800-51,200) | 800 (range: 0-12,800) |
| Time since ERT initiation | 82 weeks (range: 24-130) | 12 weeks (range: 8-24) | 38 weeks (range: 8-172) |
| Seroconversion week | 4 weeks (range: 4) | 4 weeks (range: 4-8) | 8 weeks (range: 4-64) |
| IOPD on ERT + TLD-MTX (n = 14) | | | |
| Percent | 0 | 14.2% (n = 2) | 85.7% (n = 12)** |
| Median titers (Week 12) | NA | IOPD13: 12,800; IOPD14: 25,600 | 1,600 (range: 0-12,800) |
| Median titers (Week 24) | NA | IOPD13: 12,800; IOPD14: 12,800 | 600 (range: 0-3,200) |
| Median titers (Week 52) | NA | IOPD13: 12,800 | 250*** (range: 0-800) |
| Median peak titers | NA | IOPD13: 51,200; IOPD14: 12,800 | 3,200 (range: <100-12,800) |
| Time since ERT initiation | NA | IOPD13: 7 weeks; IOPD14: 12 weeks | 20.5 weeks (range: 4-93) |
| Seroconversion week | NA | IOPD13: 3 weeks; IOPD14: 8 weeks | 6 weeks (range: 4-31) |

HSAT, high and sustained antibody titers,
SIT, sustained intermediate titers,
LT, low titers
*All patients in ERT + TLD-MTX group and 35/37 patients in ERT monotherapy group seroconverted.
**One patient had peak titers of 12,800 twice (Week 5 and Week 12) on ERT but maintained low titers throughout, so was included in LT group.
***Patients who tested seropositive but had titers <100 were deemed to have a titer of 50.

Immune Response—Transient Low-Dose Methotrexate Recipients

Figure 7:
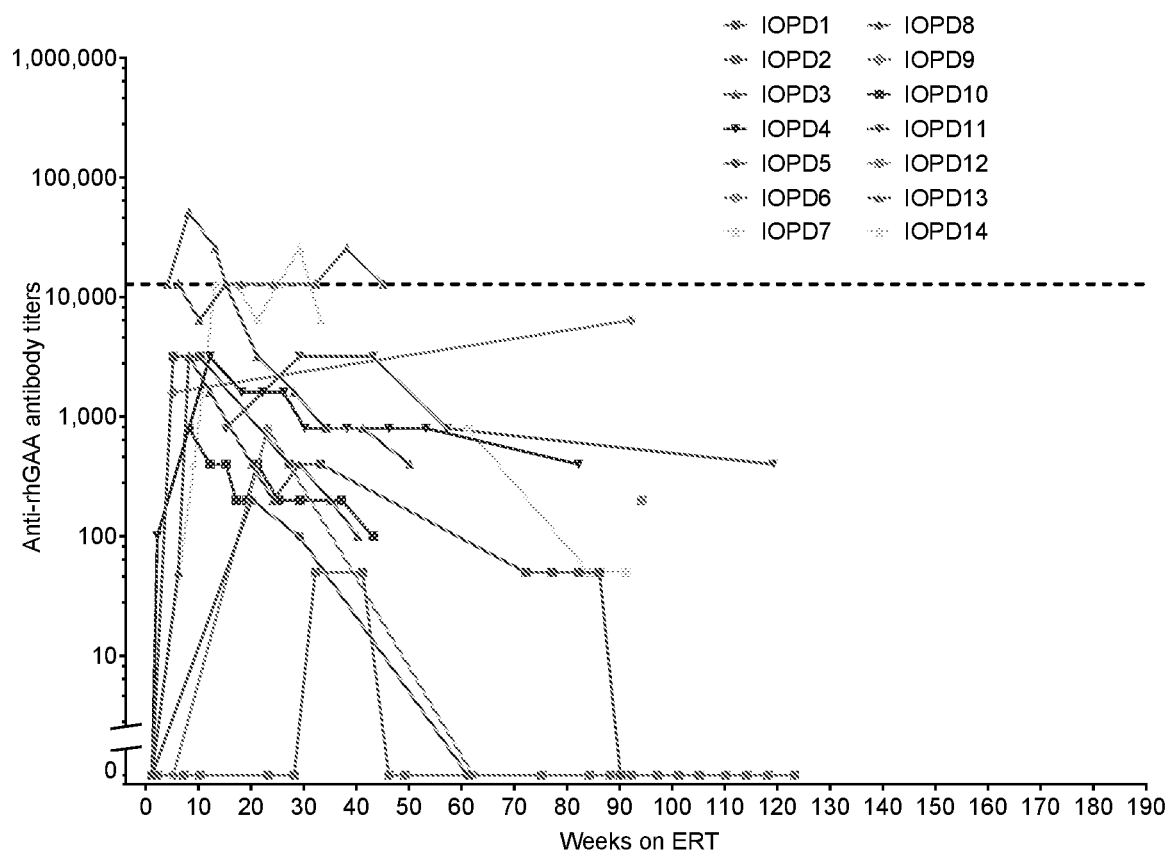
FIG. 7 is a graph showing immune response over time in the current TLD-MTX-treated CRIM-positive IOPD patients. Each patient's trajectory is graphed individually as a curve. Positive titers <100 are shown as titers of 50.

The immune response for each TLD-MTX treated patient over time is shown in FIG. 7, and summarized in Table 4 and Table 5. The median last titer was 150 (range, 0-12,800) at median time on ERT of ~71 weeks (range, 32-122 weeks). No patients who received TLD-MTX developed HSAT by the cutoff for data collection (Jun. 16, 2017). Patient IOPD13 had a titer of 51,200 at Week 7 only, decreasing to 25,600 at Weeks 12 and 37 and 12,800 at Weeks 14, 17, 23, 31, and 44. Patient IOPD14 had a titer of 25,600 at Week 28 only, and maintained titers of 12,800 at Weeks 12, 16, and 24, and 32. These 2 SIT TLD-MTX recipient patients (IOPD13 and IOPD14) had the highest titers observed in the study; the other 12 TLD-MTX recipients remained LT. One patient (IOPD2) had titers remaining <100 (seropositive on screening assay, but below the limit of titer measurement).

TABLE 5

Immune response for IOPD patients that received TLD-MTX protocol with >6 months of follow-up data available

| Patient | Peak antibody titer | Time on ERT (peak titer) (weeks) | Last antibody titer | Time on ERT (last titer) (weeks) |
|---|---|---|---|---|
| IOPD1 | 3,200 | 4 | 0 | 89 |
| IOPD2 | <100 | 31 | 0 | 122 |
| IOPD3 | 12,800* | 5 | 400 | 49 |
| IOPD4 | 3,200 | 11 | 400 | 81 |
| IOPD5 | 200 | 19 | 0 | 60 |
| IOPD6 | 800 | 22 | 0 | 61 |
| IOPD7 | 800 | 60 | <100 | 90 |
| IOPD8 | 3,200 | 7 | 100 | 39 |
| IOPD9 | 6,400 | 91 | 6,400 | 91 |
| IOPD10 | 800 | 7 | 100 | 42 |
| IOPD11 | 3,200 | 28 | 400 | 118 |
| IOPD12 | 200 | 93 | 200 | 93 |
| IOPD13 | 51,200** | 7 | 12,800 | 44 |
| IOPD14 | 25,600*** | 28 | 12.800 | 32 |
| Median | 3,200 | 20.5 | 150 | 71 |

IOPD, infantile-onset Pompe disease;
*Patient IOPD3 only received a single dose of methotrexate in cycles 2 and 3 instead of 3 doses.
**Patient IOPD13 had an increase in dose of ERT from 20 mg/kg/EOW to 40 mg/kg/EOW at Week 4 on ERT.
***Patient IOPD14 had skipped a dose of methotrexate on cycle 3.

Safety—Hematologic and Biochemical Analyses

ANC, AST, and ALT data in the first 6 weeks on ERT were available for all patients except IOPD7 (missing all 3 measures), and IOPD2 and IOPD13 (missing baseline AST and ALT). Patients IOPD1 and IOPD3 developed ANC <750 cells/mm$^3$. Patient IOPD5 developed increases exceeding three times baseline levels of both AST and ALT; patients IOPD3 and IOPD6 had such increases only in ALT. Infections around the time of TLD-MTX administration was available on nine patients. Two patients had hospitalizations related to infections around the time of methotrexate administration. One patient (IOPD8) was hospitalized for rhinovirus infection and the other patient (IOPD13) was hospitalized for concerns of underlying respiratory infections. No infections were noted in the remaining seven patients (IOPD1, IOPD5, IOPD7, IOPD9, IOPD10, IOPD12, and IOPD14).

Discussion

An ITI protocol using TLD-MTX, a brief-course (a total of 9 doses) of methotrexate in patients with CRIM-positive IOPD is described herein, which may also be considered for CRIM-negative IOPD patients lacking access to rituximab. The feasibility of implementation of this protocol was demonstrated in 13 centers in United States of America, Israel, and India, a collaboration that demonstrates how physicians can work together worldwide to leverage clinical learning in rare diseases and in this case, mitigate the deleterious impact of immune response on ERT therapy.

Brief-course, low-dose, single-drug methotrexate administered concurrently with rhGAA initiation to treatment-naïve patients with Pompe disease resulted in the cohort's median last titer of 150 (range, 0-12,800) at median time of 71 weeks (range, 32-122 weeks) of ERT. No methotrexate recipients developed HSAT by the cutoff for data collection (Jun. 16, 2017). Two patients (IOPD13 and IOPD14) had antibodies in the SIT range. Patient IOPD13 had an increase in dose of ERT from 20 mg/kg/EOW to 40 mg/kg/EOW at Week 4 on ERT. IOPD13 developed HSAT with titers peaking at 102,400 (Week 76) after the cutoff date for data collection. Bortezomib-based protocol was recommended but the parents declined. Whereas, patient IOPD14 had skipped a dose of methotrexate on cycle 3. The last titer of IOPD14 was 6,400 (Week 36) after the cutoff for the data collection. All other methotrexate recipients remained LT throughout, versus 5/37 HSAT (peak 51,200-409,600), 7/37 SIT (12,800-51,000), and 23/37 LT (200-12,800) among comparators. IOPD patients in the comparator group had a similar GAA variant profile. Importantly, all patients in this study were identified clinically and thus were symptomatic at time of diagnosis, again making the two groups very comparable. Nevertheless, cardiac or motor outcomes data were not collected, limiting the focus to ameliorating the deleterious antibody response to rhGAA. The deleterious effect of antibody titers in HSAT and SIT on cardiac and motor response has been previously published, hence cardiac or motor outcomes on these patients was not analyzed. (Kishnani et al. (2010) *Mol Genet Metab* 99:26-33; Berrier et al. (2015) *Genet Med* 17:912-918).

It is important to note that 32.4% of patients in comparator group developed HSAT or SIT vs 14.2% of patients in TLD-MTX group. It appears that, based on expectations from historical data, that TLD-MTX successfully blunted the immune response overall as demonstrated by 86.7% of patients in our cohort who maintained low titers. This patient cohort was younger, which could be more indicative of severe disease or earlier diagnosis. None of the patients was identified via newborn screening and were all clinically identified through clinical features of infantile Pompe disease including cardiomyopathy.

One of the patients was CRIM-negative, demonstrating that TLD-MTX can be attempted in CRIM-negative patients in parts of the world where ITI with rituximab is not feasible.

No serious AEs were related to methotrexate. Some patients had methotrexate doses postponed because of their clinical status. Neutropenia (ANC <750 cells/mm$^3$) affected 2 of 13 IOPD patients with ANC data (15.4%; IOPD1 and IOPD3); this was transient, and ANC returned to normal levels. Two of nine patients had hospitalizations related to infections around the time of methotrexate administration which was resolved. Overall, patients tolerated the methotrexate protocol reasonably.

This protocol uses only one-fourth to one-seventh of the methotrexate dose typical for cancer chemotherapy, and its brief time course avoids prolonged immunosuppression. Methotrexate is inexpensive and has a wide geographic availability; its lack of B-cell suppression may confer an advantageous safety profile in CRIM-positive patients as opposed to combination regimens including rituximab. (Messinger et al. (2012) *Genet. Med.* 14:135-142; Banugaria et al. (2013) *PLos One* 8:e67052). TLD-MTX is also less expensive than regimens including biologics or lengthy immunosuppression.

The data show the importance of 3 cycles of methotrexate for clinical efficacy. While 1-cycle methotrexate has not been studied systematically for ITI in humans, the patient who received only 1 cycle had a higher immune response than those who followed the 3-cycle protocol. This study did not formally compare 1 and 3 cycles (which had similar preclinical results); nonetheless, 3 cycles are beneficial at this low dose to maintain B-cell regulation, without suppressing immunity altogether, as high-dose methotrexate would.

This report of clinical ITI experience using single-drug methotrexate is confined to CRIM-positive patients, except for IOPD9, who was predicted to be CRIM-negative based on GAA variants. Further study will determine the potential applicability of this methotrexate protocol in a larger cohort of CRIM-positive patients and CRIM-negative patients in regions where rituximab is not available. The TLD-MTX protocol requires specific evaluation before being applied in CRIM-negative patients, the highest-risk group; any empirical clinical use that is attempted will provide valuable experiential data. Further study is appropriate in a larger cohort of IOPD patients, and for longer-term outcomes such as overall survival, ventilator free survival, reduction in left ventricular mass index, and urinary glucose tetrasaccharide ($Glc_4$).

Preclinical findings suggest that, TLD-MTX, which is given as a brief course at enzyme initiation (unlike ITI regimens requiring re-administration over the course of treatment), can be adaptable to other diseases treated by therapeutic enzymes. Other incipient immunomodulation methods are also being studied, such as anti-CD4 monoclonal antibodies, (Garman et al. (2004); *Clin. Exp. Imunol.* 137:496-502; Sun et al. (2014) *Mol. Genet. Metab. Rep.* 1:446-450) Tregitopes (peptides stimulating regulatory T cell expansion and activation), (Cousens et al. (2012) *Hum. Vaccin. Immunother.* 8:1459-1464) rapamycin, (Elder at al. (2013) *J. Pediatr.* 163:847-854 e841) or tolerogenic nanoparticles containing rapamycin. (Lim et al. (2017) *Mol. Genet. Metab.* 120:S83-S84).

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A method of inducing immune tolerance in a human subject suffering from Pompe disease, the method comprising:
(i) administering via infusion to a human treatment-naive subject a therapeutically effective amount of recombinant human alglucosidase alfa (rhGAA) as enzyme replacement therapy (ERT), and
(ii) administering to the subject an immune tolerance induction protocol,
wherein the immune tolerance induction protocol does not comprise administration of intravenous gamma globulin (IVIG), rituximab, or bortezomib prior to step (i);
wherein the immune tolerance induction protocol consists of a three-day cycle of methotrexate,
wherein the first day of the three-day cycle of methotrexate is the day of rhGAA administration,
wherein a dose of methotrexate comprises about 0.1 mg/kg body weight to about 0.6 mg/kg body weight per day,
wherein the methotrexate is administered either orally about one hour before the rhGAA administration or subcutaneously about 15 minutes before the rhGAA administration; and
(iii) repeating (i) and (ii) at least three times so that the subject begins a three-day cycle of methotrexate with each of the first four rhGAA infusions;
wherein, by following step (ii) and step (iii), immune tolerance to rhGAA is induced in the subject.

2. The method of claim 1, wherein the human treatment-naive subject is a cross-reactive immunological material (CRIM)-positive or a CRIM-negative Pompe patient.

3. The method of claim 1, wherein the dose of methotrexate comprises about 0.4 mg/kg body weight per day.

4. The method of claim 1,
wherein the second rhGAA infusion begins on day 14 and the second three-day cycle of methotrexate begins on day 14 of ERT and ends on day 16 of ERT,
wherein the third rhGAA infusion begins on day 28 and the third three-day cycle of methotrexate begins on day 28 of ERT and ends on day 30 of ERT, and
wherein the fourth rhGAA infusion begins on day 42 and the fourth three-day cycle of methotrexate begins on day 42 of ERT and ends on day 44 of ERT.

5. The method of claim 4, further comprising a fifth three-day cycle of methotrexate, wherein the fifth rhGAA infusion begins on day 56 and the fifth cycle of methotrexate begins on day 56 of ERT and ends on day 58 of ERT.

6. The method of claim 1,
wherein the second rhGAA infusion begins on day 7 and the second three-day cycle of methotrexate begins on day 7 of ERT and ends on day 9 of ERT, and
wherein the third rhGAA infusion begins on day 14 and the third three-day cycle begins on day 14 of ERT and ends on day 16 of ERT, and
wherein the fourth rhGAA infusion begins on day 21 and the fourth three-day cycle begins on day 21 of ERT and ends on day 23 of ERT.

7. The method of claim 6, further comprising a fifth three-day cycle of methotrexate, wherein the fifth rhGAA infusion begins on day 28 of ERT and ends on day 30 of ERT, and wherein the fifth three-day cycle of methotrexate begins on day 28 of ERT.

8. The method of claim 1, wherein the Pompe disease is infantile onset Pompe disease or late onset Pompe disease.

9. The method of claim 1, wherein the maximum daily dose of methotrexate does not exceed 7 mg when the subject weighs less than or equal to 70 kg, or wherein the maximum daily dose of methotrexate does not exceed 10 mg when the subject weighs more than 70 kg.

10. The method of claim 1, wherein formation of high and sustained antibody titers is prevented, or wherein formation of sustained intermediate titers is prevented.

11. The method of claim 1, wherein the human subject's immune tolerance to rhGAA is characterized by an IgG antibody titer of less than 12,800.

12. The method of claim 1, further comprising measuring one or more times: (i) the human subject's complete and differential blood counts and platelet levels, (ii) the level of glucose tetrasaccharide in the human subject's urine, (iii) the level of anti-rhGAA antibodies in the human subject's blood, (iv) the level of alanine aminotransferase, aspartate aminotransferase, creatine kinase, creatine kinase-MB, or any combination thereof in the human subject's blood, or (v) any combination thereof.

13. The method of claim 12, wherein the measuring occurs on the day prior to the initiation of ERT, day 7 of ERT, day 13 of ERT, day 28 of ERT, day 42 of ERT, day 56 of ERT, day 84 of ERT, day 112 of ERT, day 140 of ERT, day 168 of ERT, day 196 of ERT, day 224 of ERT, day 252 of ERT, day 280 of ERT, day 308 of ERT, day 336 of ERT, day 364 of ERT, or any combination thereof.

14. A method of inducing immune tolerance in a human subject suffering from Pompe disease, the method comprising:
   (i) administering via infusion to a human treatment-naive subject a therapeutically effective amount of recombinant human alglucosidase alfa (rhGAA) as enzyme replacement therapy (ERT), and
   (ii) administering to the subject an immune tolerance induction protocol,
      wherein the immune tolerance induction protocol does not comprise administration of intravenous gamma globulin (IVIG), rituximab, or bortezomib prior to step (i);
      wherein the immune tolerance induction protocol consists of a three-day cycle of methotrexate,
      wherein the first day of the three-day cycle of methotrexate is the day of rhGAA administration,
      wherein a dose of methotrexate comprises about 0.1 mg/kg body weight to about 0.6 mg/kg body weight per day,
      wherein the methotrexate is administered either orally about one hour before the rhGAA administration or subcutaneously about 15 minutes before the rhGAA administration; and
   (iii) repeating (i) and (ii) at least three times so that the subject receives a three-day cycle of methotrexate during each of the first four rhGAA infusions,
      wherein the second three-day cycle of methotrexate begins on day 7 of ERT, the third cycle of methotrexate begins on day 14 of ERT, and the fourth cycle of methotrexate begins on day 21 of ERT; and
      wherein, by following step (ii) and step (iii), immune tolerance to rhGAA is induced in the subject.

15. The method of claim 14, further comprising a fifth three-day cycle of methotrexate, wherein the fifth rhGAA infusion begins on day 28 and the fifth cycle of methotrexate begins on day 28 of ERT.

16. The method of claim 14, wherein formation of high and sustained antibody titers is prevented, or wherein formation of sustained intermediate titers is prevented.

17. The method of claim 14, wherein the maximum daily dose of methotrexate does not exceed 7 mg when the human subject weighs less than or equal to 70 kg, or wherein the maximum daily dose of methotrexate does not exceed 10 mg when the human subject weighs more 70 kg.

* * * * *